US008202241B2

(12) United States Patent
Karakama et al.

(10) Patent No.: US 8,202,241 B2
(45) Date of Patent: Jun. 19, 2012

(54) BLOOD PURIFICATION SYSTEM

(75) Inventors: Atsushi Karakama, Tokyo (JP);
Soichiro Okazaki, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 496 days.

(21) Appl. No.: 12/527,270

(22) PCT Filed: Feb. 14, 2008

(86) PCT No.: PCT/JP2008/052453
§ 371 (c)(1),
(2), (4) Date: Aug. 14, 2009

(87) PCT Pub. No.: WO2008/099890
PCT Pub. Date: Aug. 21, 2008

(65) Prior Publication Data
US 2010/0087771 A1    Apr. 8, 2010

(30) Foreign Application Priority Data

Feb. 15, 2007    (JP) .................................. 2007-034256

(51) Int. Cl.
*A61M 37/00*  (2006.01)
*A61M 1/00*  (2006.01)
*A61N 1/30*  (2006.01)
(52) U.S. Cl. ......... 604/6.1; 604/4.01; 604/6.01; 604/19; 604/540
(58) Field of Classification Search .............. 210/85, 210/86, 97, 103, 104, 110, 134, 137, 143, 210/252, 257.2, 321.72, 645, 646, 739, 744; 604/4.01, 6.01, 6.1, 6.11, 6.16
See application file for complete search history.

(56) References Cited

U.S. PATENT DOCUMENTS

| 5,578,223 | A | 11/1996 | Bene et al. | |
|---|---|---|---|---|
| 7,247,146 | B2 * | 7/2007 | Tonelli et al. | 604/4.01 |
| 2001/0016699 | A1 * | 8/2001 | Burbank et al. | 604/4.01 |
| 2004/0243048 | A1 * | 12/2004 | Brugger et al. | 604/4.01 |
| 2004/0243050 | A1 * | 12/2004 | Treu et al. | 604/4.01 |
| 2004/0249331 | A1 * | 12/2004 | Burbank et al. | 604/4.01 |
| 2004/0267184 | A1 * | 12/2004 | Burbank et al. | 604/6.11 |
| 2005/0045548 | A1 * | 3/2005 | Brugger et al. | 210/252 |

(Continued)

FOREIGN PATENT DOCUMENTS

EP    0722744    *  7/1996

(Continued)

OTHER PUBLICATIONS

English language Abstract of JP 3714947, Nov. 9, 2005.

(Continued)

*Primary Examiner* — Leslie Deak
*Assistant Examiner* — Xin Xie
(74) *Attorney, Agent, or Firm* — Greenblum & Bernstein P.L.C.

(57) ABSTRACT

Provision of a blood purification system comprising a blood purification tubing and a blood purification apparatus particularly suitable for use in continuous hemofiltration in which in the treatment of a patient with renal disease, multiple organ failure, and the like, the amount of water removed from the patient and the amount of supply to the patient can be more accurately controlled, and in which preparation operation is easy. A blood purification system comprising a blood purification tubing and a blood purification apparatus wherein the soft tubes of flow paths connecting a first planar panel and a second planar panel, and the location of the soft tubes are selected to satisfy a formula of a predetermined condition.

16 Claims, 17 Drawing Sheets

U.S. PATENT DOCUMENTS

| | | | |
|---|---|---|---|
| 2005/0096583 A1* | 5/2005 | Demers et al. | 604/15 |
| 2006/0084906 A1* | 4/2006 | Burbank et al. | 604/6.16 |
| 2006/0124548 A1* | 6/2006 | Okazaki | 210/646 |

FOREIGN PATENT DOCUMENTS

| | | |
|---|---|---|
| EP | 1543853 | 6/2005 |
| FR | 2397197 | 2/1979 |
| JP | 3-180309 | 8/1991 |
| JP | 9-239024 | 9/1997 |
| JP | 2000-84071 | 3/2000 |
| JP | 3413412 | 3/2003 |
| JP | 2004-313303 | 11/2004 |
| JP | 3714947 | 11/2005 |

OTHER PUBLICATIONS

English language Abstract of JP 2004-313303, Nov. 11, 2004.
English language Abstract of JP 2000-84071, Mar. 28, 2000.
English language Abstract of JP 9-239024, Sep. 16, 1997.
English language Abstract of JP 3-180309, Aug. 6, 1991.
English language Abstract of JP 3413412, Mar. 28, 2003.
Search report from E.P.O., mail date is Sep. 6, 2011.

* cited by examiner

BLOOD PURIFICATION SYSTEM

TECHNICAL FIELD

The present invention relates to a blood purification system and particularly to a blood purification system comprising a blood purification tubing and a blood purification apparatus preferred for continuous hemofiltration, continuous hemodialysis, and continuous hemodiafiltration, collectively called continuous blood purification, and plasma exchange.

BACKGROUND ART

In recent years, in the treatment of disease, such as renal disease with serious complications of the circulatory system, and multiple organ failure, blood purification, collectively called continuous blood purification, has become common and achieved clinical effects, particularly in the area of emergency and intensive care.

Continuous blood purification specifically includes continuous hemofiltration (hereinafter referred to as "CHF"), continuous hemodialysis (hereinafter referred to as "CHD"), continuous hemodiafiltration (hereinafter referred to as "CHDF"), and the like and is appropriately used according to the purpose of treatment.

Here, CHF is a method in which blood is flowed into a blood purifier that houses a semipermeable membrane to drain filtrate containing waste products from the blood through the filtration membrane, while supplying a replacement fluid into the body, and the entire process is performed continuously and slowly. Similarly, CHD is a method for continuously and slowly performing the correction of acid-base equilibrium, and the like by diffusion through a semipermeable membrane. CHDF is a combined method of the CHF and the CHD in which to improve the small molecular weight removal ability of the CHF, a dialysate is flowed on the filtrate side so as to obtain the effect of dialysis as well.

Also, as blood purification for liver failure, apheresis, or plasma exchange (hereinafter referred to as "PE"), is selected depending on the purpose of treatment and achieves clinical effects.

Here, PE is a method for removing hazardous substances metabolized and detoxified by the liver and supplying useful substances synthesized by the liver.

In any blood purification of CHF, CHD, and CHDF, as also called "continuous and slow," blood purification is performed usually in a gradual manner over several days for one treatment, which is the feature of this treatment, and this treatment is greatly different in a time scale from simple hemodialysis and hemofiltration in which one treatment time is 4 to 5 hours.

As a first preferred example of a blood purification apparatus using the continuous blood purification, Patent Document 1 (Japanese Patent Application Laid-Open No. 9-239024) describes a blood purification system comprising at least either of dialysate supplying means for hemodialysis and replacement fluid supplying means for hemofiltration, drainage means, and a blood circulation path, wherein the means respectively comprise storage containers, feed pumps, and a plurality of scales for measuring the storage containers, and wherein the flow rate of each feed pump is individually controlled, based on information from each scale.

FIG. 25 is a conceptual view showing the blood purification system using continuous blood purification in the first example described above. This blood purification system is composed of a blood drawing tubing part 81 and a blood returning tubing part 82 which constitute a blood circulation path, a drainage flow path 12 which drains water containing waste products, a replacement fluid flow path 54 connected to the blood returning tubing part 82 to inject a replacement fluid into a patient, and a dialysate flow path 35 which supplies a dialysate to the filtrate side in a blood purifier 91. A blood pump 71 is located in the blood drawing tubing part 81, and the blood purifier 91 housing a filtration membrane 92 is located between the blood drawing tubing part 81 and the blood returning tubing part 82.

The drainage flow path 12 comprises a drainage feed pump 101 which drains a filtrate and a dialysis drainage from the blood purifier 91, a drainage storage container 141 connected to a drainage flow path 17 branching off on the outlet side of the drainage feed pump 101, and a drainage blocking valve 111 attached to a drainage flow path 13 on the downstream side of the branch part. Also, a scale for drainage measurement 151 is provided on the drainage storage container 141.

The dialysate flow path 35 comprises a feed pump 102 for a dialysate which supplies the dialysate to the filtrate side in the blood purifier 91, a dialysate storage container 142 connected to a dialysate flow path 37 branching off on the inlet side of the dialysate feed pump 102, and a dialysate supply blocking valve 112 attached to a dialysate flow path 32 on the upstream side of the branch part. A scale for dialysate measurement 152 is provided on the dialysate storage container 142.

The replacement fluid flow path 54 comprises a replacement fluid feed pump 103 which supplies the replacement fluid to the patient, a replacement fluid storage container 143 connected to a replacement fluid flow path 57 branching off on the inlet side of the replacement fluid feed pump 103, and a replacement fluid supply blocking valve 113 attached to a replacement fluid flow path 52 on the upstream side of the branch part. A scale for replacement fluid measurement 153 is provided on the replacement fluid storage container 143.

Blood taken out of the patient by the blood pump 71 passes through the blood drawing tubing part 81 and is introduced into the blood purifier 91 in which the filtration membrane 92 is housed, and waste products and the like are removed. In the blood purifier 91, the dialysate is supplied by the dialysate feed pump 102 for acid-base equilibrium and the like, and the filtrate and the dialysis drainage are drained by the drainage feed pump 101. When the blood subjected to filtration and dialysis in the blood purifier 91 is returned to the patient through the blood returning tubing part 82, the replacement fluid is added to the blood by the replacement fluid feed pump 103, and the blood is injected into the patient.

This system is advantageous in that treatment can be safely continued while the amount of the body fluid of the patient is suitably controlled without requiring frequent measurement and adjustment operations by a staff. Further, this system is advantageous in that the replacement of a dialysate storage part 121 and a replacement fluid storage part 122, and the replacement of a tank in the case where the filtrate and the dialysis drainage are stored in the tank or the like, can be performed at any time without directly affecting the measurement of the amount of water removed and without stopping treatment.

The feed pump has some feed error. To reduce the effect of the error as much as possible, in the above system, the scales 151, 152, and 153 are located on the storage containers 141, 142, and 143 respectively, and data from the scales are fed to a controller not shown. The controller constantly monitors the data of the scales 151, 152, and 153 and calculates an actual flow rate from a change in weight per unit time. When there is a difference between the actual flow rate and a set flow rate, the number of revolutions of motors for the feed pumps 101, 102, and 103 is individually automatically adjusted, and controlled so that the set flow rate and the actual flow rate are equal, thereby maintaining flow rate precision.

The above-described system can maintain high flow rate precision, but due to factors, such as the temperature characteristics of the weight sensor and the electronic circuit for measurement, change over time, the method of adjustment used during manufacture, and a change in the shape of each storage container, it is inevitable that each feed pump has flow rate precision with an error of about 1% in actual operation.

As described above, the amount of water removed for a patient with renal failure is controlled as an important parameter, and the amount of water removed ΔV (L) is obtained by the following formula (1).

$$\Delta V = VF - VC - VD \quad (1)$$

In the formula (1), VF (L) is the amount of the drainage drained by the drainage feed pump 101, VC (L) is the amount of the replacement fluid supplied by the replacement fluid feed pump 103, and VD (L) is the amount of the dialysate supplied by the dialysate feed pump 102.

Conventionally, in performing the treatment of the CHDF, the feed pump is generally used at a flow rate of about 1 L/h. For example, when the flow rate of the drainage feed pump 101 is set at 1 L/h, the flow rate of the replacement fluid feed pump 103 is set at 0.5 L/h, and the flow rate of the dialysate feed pump 102 is set at 0.5 L/h, and when the flow rate error of each feed pump is about 1%, VF=24±0.24 (L), VC=12±0.12 (L), and VD=12±0.12 (L) are provided in 24 hours. When the amount of water removed ΔV is calculated, based on the formula (1), ΔV=0±0.48 (L) is provided, so that the error of water removed can be reduced to about 0.48 (L), corresponding to 2% of the amount of the drainage VF, or less. This theory also applies to systems shown in Patent Document 2 (Japanese Patent No. 3180309) and Patent Document 3 (Japanese Patent No. 3413412), in which the flow rate error of each pump is also about 1%.

On the other hand, in recent years, in performing the treatment of CHDF or the like, the case where the treatment is performed with a high flow rate of the feed pump, to perform the treatment more efficiently, has been increasing. In this case, with a system in which the flow rate error of each feed pump is about 1% as in a conventional system, for example, when the flow rate of the drainage feed pump 101 is set at 5 L/h, the flow rate of the replacement fluid feed pump 103 is set at 2.5 L/h, and the flow rate of the dialysate feed pump 102 is set at 2.5 L/h, and when the flow rate error of each feed pump is about 1%, VF=120±1.2 (L), VC=60±0.6 (L), and VD=60±0.6 (L) are provided in 24 hours. When the amount of water removed ΔV is calculated, based on the formula (1), ΔV=0±2.4 (L) is provided, so that the error of water removed is as much as about 2.4 L, corresponding to 2% of the amount of the drainage VF.

With such a large error, a problem may be that a risk that the balance of the body fluid of the patient is abnormal is greater than the treatment effect of blood purification. To solve this problem, as a second example, a system in Patent Document 4 (Japanese Patent No. 3714947) comprises dialysate supplying means for hemodialysis, replacement fluid supplying means for hemofiltration, drainage means, and a blood circulation path, wherein the means respectively comprise storage containers and feed pumps, and comprise one scale for simultaneously measuring the three storage containers. The blood purification system wherein the flow rate of each feed pump is individually controlled, based on information from this scale is described.

FIG. 26 is a conceptual view showing the blood purification system using continuous blood purification in the second example described above. In this blood purification system, a scale 154 which simultaneously measures three storage containers, a drainage storage container 141, a dialysate storage container 142, and a replacement fluid storage container 143, is provided. It is reported that the error of water removed is reduced to about 0.5% of VF because the amount of water removed ΔV in the formula (1) is measured by the scale 154.

In the area of emergency medical care and intensive care, the treatment of CHDF and the like has become general, and the case where the treatment is performed with the flow rate of the feed pump being a high flow rate of about 10 L/h, to perform the treatment more efficiently, also has been increasing. The system in Patent Document 4 has a great feature that the error of water removed can be reduced. However, since the system configuration is complicated, further improvement has been required. To mount in the apparatus the blood tubing branching off in a complicated manner, complicated operations are necessary, and particularly, the operator is required to reliably mount a portion associated with the storage container because it directly affects the result of measurement. However, any of a drainage flow path 17, a dialysate flow path 37, and a replacement fluid flow path 57 connected to the measurement container is mounted twisted, pulled, or with the ducts crossed, or the like, so that measurement may be affected.

Patent Document 1: Japanese Patent Application Laid-Open No. 9-239024
Patent Document 2: Japanese Patent No. 3180309
Patent Document 3: Japanese Patent No. 3413412
Patent Document 4: Japanese Patent No. 3714947

DISCLOSURE OF THE INVENTION

Problems to be Solved by the Invention

The present invention has been made in view of such problems, and it is an object of the present invention to provide a blood purification system comprising a blood purification tubing and a blood purification apparatus particularly suitable for use in continuous hemofiltration, in which in the treatment of a patient with renal disease, multiple organ failure, and the like, the amount of water removed from the patient and the amount of supply to the patient can be more accurately controlled, and in which preparation operation is easy.

Means for Solving the Problems

As a result of diligent study to solve the above problems, the present inventors have found that the problems can be solved by dividing into three groups, a group of storage containers comprising a drainage storage container, a dialysate storage container, and a replacement fluid storage container, a group of flow paths comprising a drainage flow path, a dialysate flow path, and a replacement fluid flow path connected to the storage containers, and a group of flow paths at ends on the sides opposite to the storage container sides of the flow paths, and respectively integrating the group of storage containers and the groups of flow paths and connecting them with a group of flow paths of soft tubes, and have completed the present invention. In other words, the present invention comprises the following inventions.

(1) A blood purification system comprising a blood purification tubing and a blood purification apparatus, wherein the blood purification tubing has a blood drawing tubing part for feeding blood drawn from a patient to a blood purifier, a blood returning tubing part for returning blood in the blood purifier to the patient, a dialysate supplying tubing part for supplying a dialysate to the blood purifier, a drainage tubing part for performing drainage from the blood purifier, and a replacement fluid supplying tubing part for supplying a replacement fluid to the blood drawing tubing part or the blood returning tubing part, the dialysate supplying tubing part has a dialysate storage container, the drainage tubing part has a drainage storage container, the replacement fluid supplying tubing part has a replacement fluid storage container, the dialysate supplying tubing part, the drainage tubing part, and the replacement fluid supplying tubing part are each located to pass in a first planar panel and in a second planar panel, the dialysate storage container, the drainage storage container, and the replacement fluid storage container are installed in the second planar panel, flow paths connecting the first planar panel and the second planar panel, in the dialysate supplying tubing part, the drainage tubing part, and the replacement fluid supplying tubing part, are composed of a soft tube, the blood purification apparatus has a scale for measuring the second planar panel, and the soft tubes and location of the soft tubes are selected to satisfy the following formulas (1) and (2) when a weight of the second planar panel, with the three storage containers being empty, is B, a value obtained by subtracting the weight B from a weight of the second planar panel, with a liquid having a weight W placed only in the drainage storage container, is Wf, a value obtained by subtracting the weight B from a weight of the second planar panel, with a liquid having the weight W placed only in the dialysate storage container, is Wd, and a value obtained by subtracting the weight B from a weight of the second planar panel, with a liquid having the weight W placed only in the replacement fluid storage container, is Wr, and when each weight of B, Wf, Wd, and Wr is obtained from a numerical value measured by the scale of the blood purification apparatus.

$$|Wf-Wr|/W \leq 0.005 \quad (1)$$

$$|Wf-Wd|/W \leq 0.005 \quad (2)$$

(2) The blood purification system according to (1), wherein one end side of the soft tube is connected at an end α on the second planar panel, and the other end side is connected at an end β on the first planar panel, and the soft tube is located so that when an axial direction in an arbitrary portion χ in a longitudinal direction of the soft tube connecting the end α and the end β is a vector X, a gravity direction is a vector G, and a narrower angle formed by the vector X and the vector G is an angle θX, at least one portion χ in which the angle θX is 70° to 110° is present, provided that the vector X is a direction from the second planar panel toward the first planar panel.

(3) The blood purification system according to (1) or (2), wherein the blood purification tubing further has a dialysate feed pump tube, a replacement fluid feed pump tube, and a drainage feed pump tube, the blood purification apparatus further has a dialysate feed pump, a replacement fluid feed pump, and a drainage feed pump for squeezing the pump tubes for feeding, in the dialysate supplying tubing part, the dialysate feed pump tube, a dialysate branch duct, and a dialysate supply blocking part are located in this order from a dialysate inlet side of the blood purifier on a tubing having one end side connected to a dialysate inlet of the blood purifier and the other end side connected to a dialysate storage part, and the dialysate storage container is connected to the dialysate branch duct, in the replacement fluid supplying tubing part, the replacement fluid feed pump tube, a replacement fluid branch duct, and a replacement fluid supply blocking part are located in this order from a blood returning tubing part or blood drawing tubing part side on a tubing having one end side connected to the blood returning tubing part or the blood drawing tubing part and the other end side connected to a replacement fluid storage part, and the replacement fluid storage container is connected to the replacement fluid branch duct, in the drainage tubing part, the drainage feed pump tube, a drainage branch duct, and a drainage blocking part are located in this order from a drainage outlet side of the blood purifier on a tubing having one end side connected to a drainage outlet of the blood purifier and the other end side open, and the drainage storage container is connected to the drainage branch duct, the blood purification apparatus further has a dialysate supply blocking valve, a replacement fluid supply blocking valve, and a drainage blocking valve for blocking the blocking parts, a flow path in a portion near the dialysate feed pump tube and between the dialysate inlet of the blood purifier and the dialysate feed pump tube, and a flow path in a portion near the dialysate feed pump tube and between the dialysate feed pump tube and an end connected to the dialysate storage part, in the dialysate supplying tubing part, a flow path in a portion near the replacement fluid feed pump tube and between an end connected to the blood returning tubing part or the blood drawing tubing part and the replacement fluid feed pump tube, and a flow path in a portion near the replacement fluid feed pump tube and between the replacement fluid feed pump tube and an end on the side connected to the replacement fluid storage part, in the replacement fluid supplying tubing part, and a flow path in a portion near the drainage feed pump tube and between the drainage outlet of the blood purifier and the drainage feed pump tube, and a flow path in a portion near the drainage feed pump tube and between the drainage feed pump tube and an open end, in the drainage tubing part are installed in the first planar panel, the dialysate feed pump tube, the replacement fluid feed pump tube, and the drainage feed pump tube are connected to the first planar panel, and the dialysate branch duct, the replacement fluid branch duct, and the drainage branch duct are installed in the first planar panel or the second planar panel.

(4) The blood purification system according to (3), wherein the blood purification apparatus has a heating apparatus, the flow path in the portion near the dialysate feed pump tube and between the dialysate inlet of the blood purifier and the dialysate feed pump tube in the dialysate supplying tubing part, installed in the first planar panel, is a dialysate heating flow path, the flow path in the portion near the replacement fluid feed pump tube and between the end connected to the blood returning tubing part or the blood drawing tubing part and the replacement fluid feed pump tube in the replacement fluid supplying tubing part, installed in the first planar panel, is a replacement fluid heating flow path, and at least one surface of the dialysate heating flow path and the replacement fluid heating flow path is in contact with a heater surface of the heating apparatus.

(5) The blood purification system according to (3) or (4), wherein the dialysate feed pump, the replacement fluid feed pump, and the drainage feed pump are tubing pumps, and a plane of an orbit in which a roller revolves, and a planar part of the first planar panel are located at a generally right angle.

(6) The blood purification system according to any of (3) to (5), wherein having a fixture for fixing a part on an inlet side and/or outlet side of any of the dialysate feed pump tube, the replacement fluid feed pump tube, and the drainage feed pump tube.

(7) A blood purification system comprising a blood purification tubing and a blood purification apparatus, wherein the blood purification tubing has a blood drawing tubing part for feeding blood drawn from a patient to a blood purifier, a blood returning tubing part for returning blood in the blood purifier to the patient, a drainage tubing part for performing drainage from the blood purifier, and a replacement fluid supplying tubing part for supplying a replacement fluid to the blood drawing tubing part or the blood returning tubing part, the drainage tubing part has a drainage storage container, the replacement fluid supplying tubing part has a replacement fluid storage container, the drainage tubing part and the replacement fluid supplying tubing part are each located to pass in a first planar panel and in a second planar panel, the drainage storage container and the replacement fluid storage container are installed in the second planar panel, flow paths connecting the first planar panel and the second planar panel, in the drainage tubing part and the replacement fluid supplying tubing part, are composed of a soft tube, the blood purification apparatus has a scale for measuring the second planar panel, and the soft tubes and location of the soft tubes are selected to satisfy the following formula (1) when a weight of the second planar panel, with the drainage storage container and the replacement fluid storage container being empty, is B, a value obtained by subtracting the weight B from a weight of the second planar panel, with a liquid having a weight W placed only in the drainage storage container, is Wf, and a value obtained by subtracting the weight B from a weight of the second planar panel, with a liquid having the weight W placed only in the replacement fluid storage container, is Wr, and when each weight of B, Wf, and Wr is obtained from a numerical value measured by the scale of the blood purification apparatus.

$$|Wf - Wr|/W \leq 0.005 \quad (1)$$

(8) The blood purification system according to (7), wherein another container is located in the second planar panel, and the weight B is weight when the two storage containers and the another container of the second planar panel are empty.

(9) The blood purification system according to (8), wherein the another container is connected to the replacement fluid storage container.

(10) The blood purification system according to (8) or (9), wherein a flow path for forming a dialysate supplying tubing part for supplying a dialysate to the blood purifier is formed in the first planar panel.

(11) The blood purification system according to any of (7) to (10), wherein one end side of the soft tube is connected at an end α on the second planar panel, and the other end side is connected at an end β on the first planar panel, and the soft tube is located so that when an axial direction in an arbitrary portion χ in a longitudinal direction of the soft tube connecting the end α and the end β is a vector X, a gravity direction is a vector G, and a narrower angle formed by the vector X and the vector G is an angle θX, at least one portion χ in which the angle θX is 70° to 110° is present, provided that the vector X is a direction from the second planar panel toward the first planar panel.

(12) The blood purification system according to any of (7) to (11), wherein the blood purification tubing further has a replacement fluid feed pump tube and a drainage feed pump tube, the blood purification apparatus further has a replacement fluid feed pump and a drainage feed pump for squeezing the pump tubes for feeding, in the replacement fluid supplying tubing part, the replacement fluid feed pump tube, a replacement fluid branch duct, and a replacement fluid supply blocking part are located in this order from a blood returning tubing part or blood drawing tubing part side on a tubing having one end side connected to the blood returning tubing part or the blood drawing tubing part and the other end side connected to a replacement fluid storage part, and the replacement fluid storage container is connected to the replacement fluid branch duct, in the drainage tubing part, the drainage feed pump tube, a drainage branch duct, and a drainage blocking part are located in this order from a drainage outlet side of the blood purifier on a tubing having one end side connected to a drainage outlet of the blood purifier and the other end side open, and the drainage storage container is connected to the drainage branch duct, the blood purification apparatus further has a replacement fluid supply blocking valve and a drainage blocking valve for blocking the blocking parts, a flow path in a portion near the replacement fluid feed pump tube and between an end connected to the blood returning tubing part or the blood drawing tubing part and the replacement fluid feed pump tube, and a flow path in a portion near the replacement fluid feed pump tube and between the replacement fluid feed pump tube and an end on the side connected to the replacement fluid storage part, in the replacement fluid supplying tubing part, and a flow path in a portion near the drainage feed pump tube and between the drainage outlet of the blood purifier and the drainage feed pump tube, and a flow path in a portion near the drainage feed pump tube and between the drainage feed pump tube and an open end, in the drainage tubing part are installed in the first planar panel, the replacement fluid feed pump tube and the drainage feed pump tube are connected to the first planar panel, and the replacement fluid branch duct and the drainage branch duct are installed in the first planar panel or the second planar panel.

(13) The blood purification system according to (12), wherein the blood purification apparatus has a heating apparatus, the flow path in the portion near the replacement fluid feed pump tube and between the end connected to the blood returning tubing part or the blood drawing tubing part and the replacement fluid feed pump tube in the replacement fluid supplying tubing part, installed in the first planar panel, is a replacement fluid heating flow path, and at least one surface of the replacement fluid heating flow path is in contact with a heater surface of the heating apparatus.

(14) The blood purification system according to (12) or (13), wherein the replacement fluid feed pump and the drainage feed pump are tubing pumps, and a plane of an orbit in which a roller revolves, and a planar part of the first planar panel are located at a generally right angle.

(15) The blood purification system according to any of (12) to (14), wherein having a fixture for fixing a part on the inlet side and/or outlet side of any of the replacement fluid feed pump tube and the drainage feed pump tube.

(16) The blood purification system according to any of (1) to (15), wherein the first planar panel is an integral plastic molding or one in which plastic moldings are bonded and integrated.

Advantages of the Invention

According to the present invention, the error of the amount of water removed, which is the most important parameter for patient control, is reduced to about 0.5% of the amount of the drainage drained by the drainage feed pump, so that control can be performed with precision four times higher than conventional one. Furthermore, conventionally, complicated operations for the preparation of treatment are necessary, and when only several treatments are performed per month, even only the operation of mounting the blood tubing in the apparatus takes as long as about 30 minutes, but the time for the operation is reduced to about 5 minutes by the present invention. Also, an increase in measurement error due to improper mounting is eliminated, so that treatment with high reliability can be performed.

BRIEF DESCRIPTION OF THE DRAWINGS

FIG. 9 is a schematic view showing another example of the location of the flow paths spanning the first planar panel and the second planar panel in the blood purification system according to the present invention.

DESCRIPTION OF SYMBOLS

Figure 1:
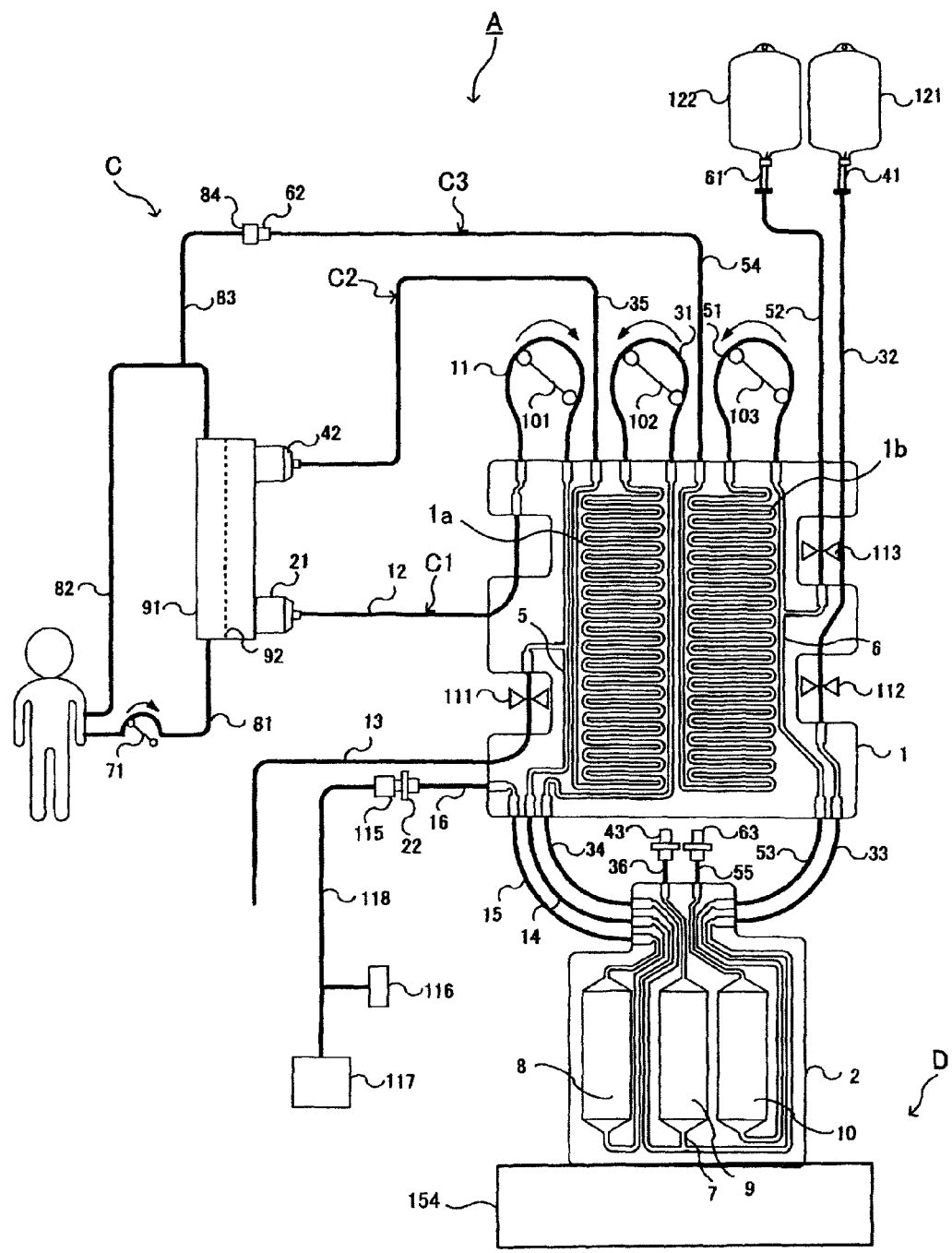
FIG. 1 is a schematic view showing one embodiment of the blood purification system according to the present invention.

1 . . . first planar panel
1a . . . first dialysate inner flow path
1b . . . first replacement fluid inner flow path
2 . . . second planar panel
5 . . . drainage branch duct
6 . . . replacement fluid branch duct
7 . . . dialysate branch duct
8 . . . drainage storage container
9 . . . dialysate storage container
10 . . . replacement fluid storage container
11 . . . drainage feed pump tube
31 . . . dialysate feed pump tube
51 . . . replacement fluid feed pump tube
12 to 17 . . . drainage flow path
32 to 37 . . . dialysate flow path
52 to 55, 57, 58 . . . replacement fluid flow path
56 . . . coupling tube
71 . . . blood pump
81 . . . blood drawing tubing part
82 . . . blood returning tubing part
91 . . . blood purifier
93 . . . membrane type plasma separator
101 . . . drainage feed pump
102 . . . dialysate feed pump
103 . . . replacement fluid feed pump
111 . . . drainage blocking valve (part)
112 . . . dialysate supply blocking valve (part)
113, 114 . . . replacement fluid supply blocking valve (part)
116 . . . air valve
117 . . . air pump
118 . . . tubing
121 . . . dialysate storage part
122 . . . replacement fluid storage part
131 . . . roller
133 . . . rotor
135 . . . stator
151 . . . scale for drainage measurement
152 . . . scale for dialysate measurement
153 . . . scale for replacement fluid measurement
154 . . . scale
A . . . blood purification system
C . . . blood purification tubing
C1 . . . drainage tubing part
C2 . . . dialysate supplying tubing part
C3 . . . replacement fluid supplying tubing part
D . . . blood purification apparatus

BEST MODE FOR CARRYING OUT THE INVENTION

Figure 25:
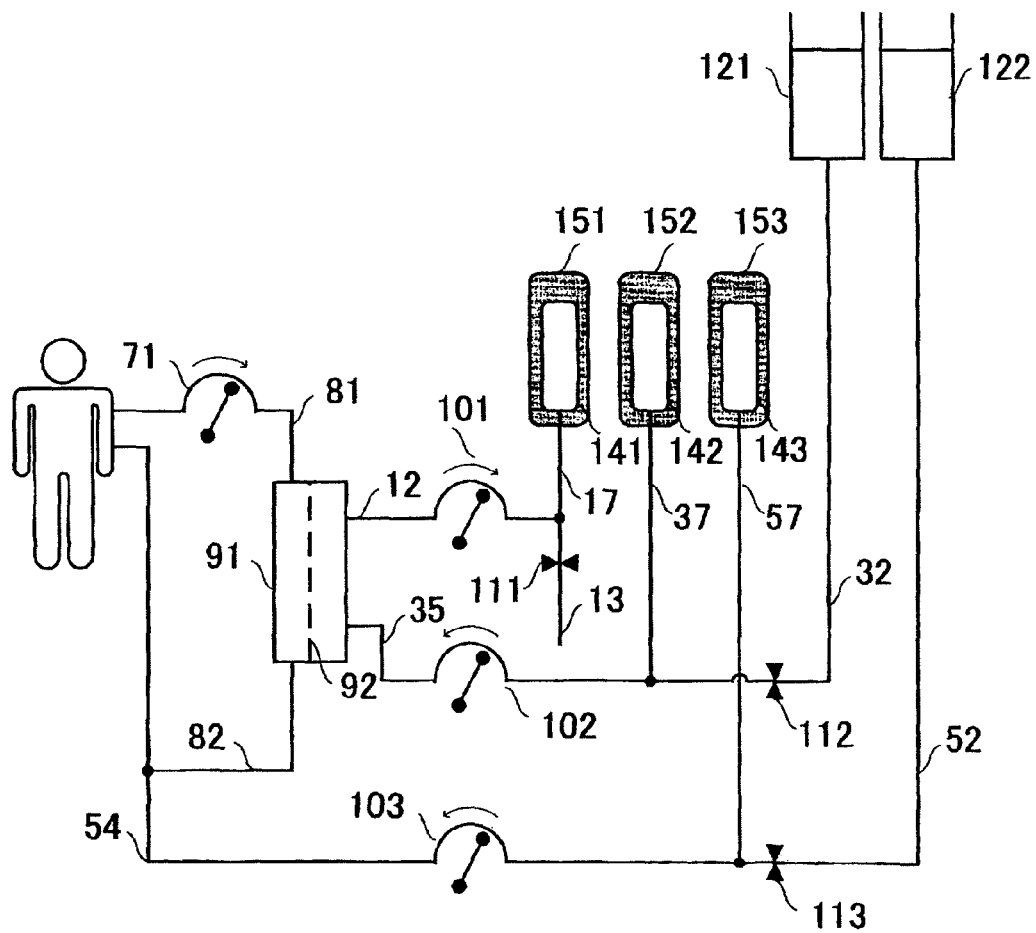
FIG. 25 is a schematic view showing a first example of a conventional blood purification system.
Figure 26:
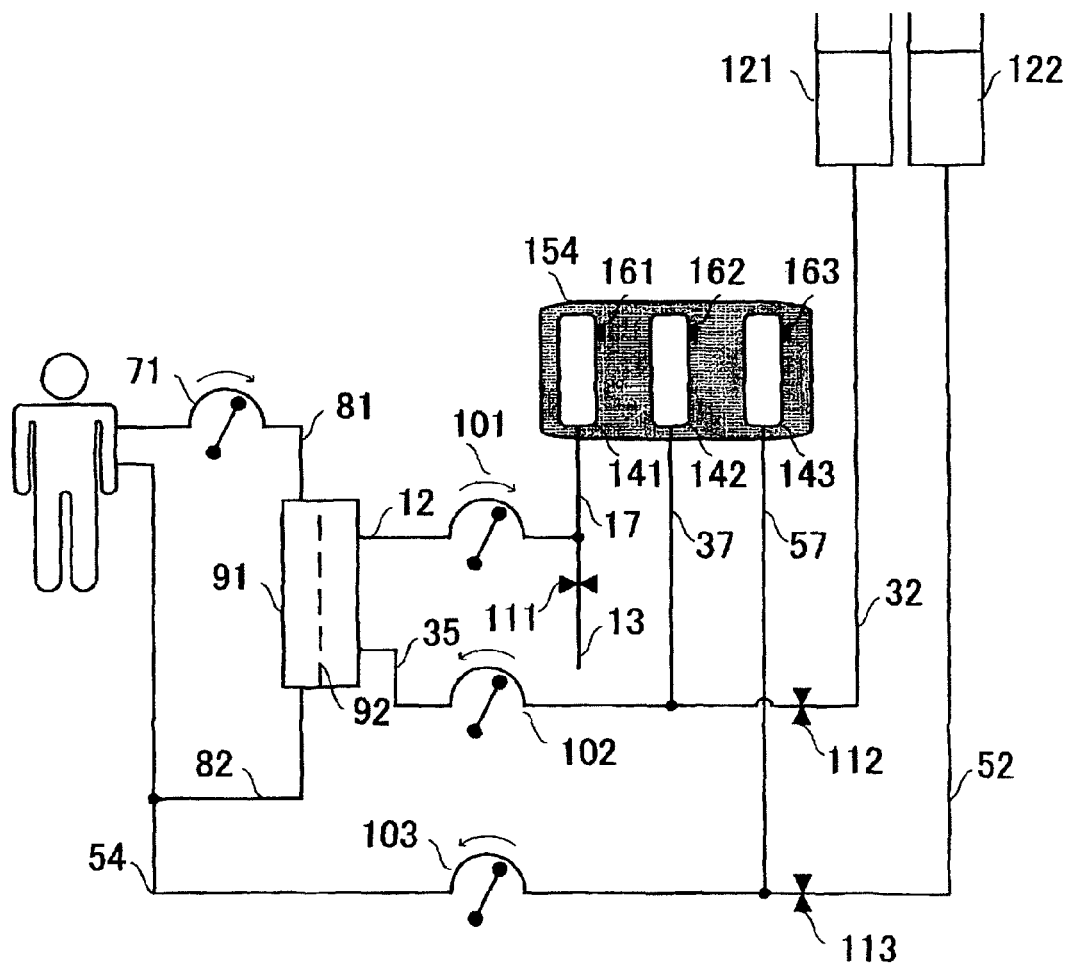
FIG. 26 is a schematic view showing a second example of the conventional blood purification system.

The blood purification system according to the present invention will be described below, based on embodiments, with reference to the drawings. FIG. 1 shows one embodiment of the blood purification system according to the present invention. This system is a blood purification system using continuous hemodiafiltration (CHDF) combining continuous hemofiltration (CHF) and continuous hemodialysis (CHD), basically similar to that shown in FIG. 25. In the figures, constituent members in the figures having the same functions as constituent members are referred to by the same numerals.

This blood purification system A has a blood purification tubing C and a blood purification apparatus D. The blood purification tubing C has, for example, a blood drawing tubing part 81 and a blood returning tubing part 82 which constitute a blood circulation path, a drainage tubing part C1 which drains water containing waste products from a blood purifier 91, a dialysate supplying tubing part C2 which supplies a dialysate to the filtrate side in the blood purifier 91, and a replacement fluid supplying tubing part C3 connected to the blood returning tubing part 82 to inject a replacement fluid into a patient. The drainage tubing part C1, the dialysate supplying tubing part C2, and the replacement fluid supplying tubing part C3 are each formed to pass through a first planar panel 1 and a second planar panel 2. A blood pump 71 is located in the blood drawing tubing part 81, and the blood purifier 91 housing a filtration membrane 92 is located between the blood drawing tubing part 81 and the blood returning tubing part 82. In the drainage tubing part C1, the blood purifier 91 and the first planar panel 1 are connected by a drainage flow path 12. In the replacement fluid supplying tubing part C2, a branch flow path 83 branches off from the blood returning tubing part 82, and the branch flow path 83 and the first planar panel 1 are connected by a replacement fluid flow path 54. In the dialysate supplying tubing part C3, the blood purifier 91 and the first planar panel 1 are connected by a dialysate flow path 35.

A drainage feed pump tube 11 which drains a filtrate and a dialysis drainage from the blood purifier 91, a dialysate feed pump tube 31 which supplies the dialysate to the filtrate side in the blood purifier 91, and a replacement fluid feed pump tube 51 which supplies the replacement fluid to the patient are each connected liquid-tight to the first planar panel 1. The inlet side of the drainage feed pump tube 11 is connected to the drainage flow path 12 via the first planar panel 1. The end of the drainage flow path 12 is connected to a connector 21 for connection to the blood purifier 91, and the connector 21 is connected to the blood purifier 91. The outlet side of the drainage feed pump tube 11 is connected to a drainage inner flow path in the first planar panel 1, and in the drainage inner flow path, a drainage branch duct 5 branches off from a drainage main duct. The drainage main duct is connected to a drainage flow path 13 outside the first planar panel 1. A drainage blocking valve (part) 111 is provided in the drainage flow path 13, and the end of the drainage flow path 13 is open. The other, the drainage branch duct 5, is connected to a drainage flow path 14 outside the first planar panel 1. The drainage flow path 14 is connected to the second planar panel 2.

The first planar panel 1 and the second planar panel 2 are plastic moldings in which liquid passages are formed. Two flat plate-shaped flow path molded parts in which liquid passages are formed may be bonded to each other, and the planar panel can also be manufactured by bonding two, a flat plate-shaped flow path molded part in which liquid passages are formed, and a flat plate. Also, the planar panel can be manufactured by blow molding.

For the first planar panel 1 and the second planar panel 2, a material having biocompatibility and biological safety is preferred because the body fluid of the patient is in direct or indirect contact with the planar panel. As the material, synthetic resins, particularly thermoplastic resins, are preferred in terms of manufacturing cost, processability, and operability. As the thermoplastic resins, polyolefin resins, polyamide resins, polyester resins, polyurethane resins, fluorine resins, silicon resins, and the like, and further, ABS (acrylonitrile-butadiene-styrene copolymer) resins, polyvinyl chloride, polycarbonate, polystyrene, polyacrylate, polyacetal, and the like can be illustrated. Any of them can be preferably used. When the material is a hard plastic, the shape of the flow path is not deformed, even if the liquid flowing in the tubing is under negative pressure, and contact with the heater surface of a heating apparatus described later is sufficient, so that a decrease in heating ability does not occur. Also, since the deformation of the shape of the flow path does not occur, a change in the flow rate of the liquid also does not occur. For these reasons, the plastic used in the present invention is preferably hard.

An inner flow path having one end leading to the above drainage flow path 14 is formed in the second planar panel 2, and a drainage storage container 8 which stores the drainage is formed in the inner flow path. The other end of the inner flow path passing through this drainage storage container 8 is connected to a drainage flow path 15 outside the second planar panel 2. The drainage flow path 15 is connected to the first planar panel 1, and connected to a drainage flow path 16 outside the first planar panel 1 via the first planar panel 1. A transducer protection filter 22 is connected to the other end of the drainage flow path 16. The transducer protection filter 22 is connected to a connection part 115. The connection part 115 is connected to a tubing 118. The tubing 118 branches off, and one is connected to an air valve 116. The other branching tubing is connected to an air pump 117.

The outlet side of a dialysate feed pump 102 is connected to a zigzag, first dialysate inner flow path 1a in the first planar panel 1, and connected to the above dialysate flow path 35 via the first dialysate inner flow path 1a. The end of the dialysate flow path 35 is connected to a connector 42 for connection to the blood purifier 91, and the connector 42 is connected to the blood purifier 91.

The inlet side of the dialysate feed pump 102 is connected to a second dialysate inner flow path in the first planar panel 1, and connected to a dialysate flow path 34 outside the first planar panel 1 via the second dialysate inner flow path. The dialysate flow path 34 is connected to the second planar panel 2. An inner flow path having one end leading to the above dialysate flow path 34 is formed in the second planar panel 2, and in the inner flow path, a dialysate branch duct 7 branches off from a dialysate main duct in the lower part of the second planar panel 2. A dialysate storage container 9 which stores the dialysate is formed in the dialysate branch duct 7. This dialysate storage container 9 is in communication with a dialysate flow path 36 connected to the upper part of the second planar panel 2, and a transducer protection filter 43 is connected to the other end of the dialysate flow path 36. The dialysate main duct is connected to a dialysate flow path 33 outside the second planar panel 2. The dialysate flow path 33 is connected to the first planar panel 1, and is further connected to a dialysate flow path 32 outside the first planar panel 1 via the first planar panel 1. A plastic needle 41 is connected to the other end of the dialysate flow path 32. The plastic needle 41 is connected to a dialysate storage part (bag) 121 in which the dialysate is stored.

The outlet side of a replacement fluid feed pump 103 is connected to a zigzag, first replacement fluid inner flow path 1b in the first planar panel 1, and connected to the above replacement fluid flow path 54 via the first replacement fluid inner flow path 1b. A male connector 62 is provided at the end of the replacement fluid flow path 54 and connected to a female connector 84. The female connector 84 is connected to the branch flow path 83 branching off from the blood returning tubing part 82.

The inlet side of the replacement fluid feed pump 103 is connected to a second replacement fluid inner flow path in the first planar panel 1. In the second replacement fluid inner flow path, a replacement fluid branch duct 6 branches off from a replacement fluid main duct, and the branching replacement fluid branch duct 6 is connected to a replacement fluid flow path 53 outside the first planar panel 1. The other end of the replacement fluid flow path 53 is connected to the second planar panel 2. An inner flow path having one end leading to the above replacement fluid flow path 53 is formed in the second planar panel 2, and a replacement fluid storage container 10 which stores the replacement fluid is formed in the inner flow path. The replacement fluid storage container 10 is in communication with a replacement fluid flow path 55 connected to the upper part of the second planar panel 2, and a transducer protection filter 63 is connected to the other end of the replacement fluid flow path 55. The replacement fluid main duct of the second replacement fluid inner flow path in the first planar panel 1 is connected to a replacement fluid flow path 52 outside the first planar panel 1. A plastic needle 61 is connected to the other end of the replacement fluid flow path 52. The plastic needle 61 is connected to a replacement fluid storage part (bag) 122 in which the replacement fluid is stored.

Also for the material of the drainage flow paths of the drainage tubing part C1, the dialysate flow paths of the dialysate supplying tubing part C2, the replacement fluid flow paths of the replacement fluid supplying tubing part C3, and the pump tubes 11, 31, and 51 of the feed pumps 101, 102, and 103, synthetic resins, particularly thermoplastic resins, are preferred in terms of manufacturing cost, processability, and operability. As the thermoplastic resins, polyolefin resins, polyamide resins, polyester resins, polyurethane resins, fluorine resins, silicon resins, and the like, and further, ABS (acrylonitrile-butadiene-styrene copolymer) resins, polyvinyl chloride, polycarbonate, polystyrene, polyacrylate, polyacetal, and the like can be illustrated. Any of them can be preferably used. Particularly, soft materials are preferred because they are resistant to folding, cracking, and the like, and have excellent flexibility during operation, and for reasons of assembly properties, soft vinyl chloride is particularly preferred. Therefore, in this embodiment, soft tubes are used for the drainage flow paths 12, 13, 14, and 15 of the drainage tubing part C1, the dialysate flow paths 32, 33, 34, 35, and 36 of the dialysate supplying tubing part C2, the replacement fluid flow paths 52, 53, 55, and 54 of the replacement fluid supplying tubing part C3, the pump tubes 11, 31, and 51, and the like.

The blood purification apparatus D has a scale 154, and the second planar panel 2 is fixed and held on one scale 154 and measured. Further, the blood purification apparatus D has a heating apparatus, and the first dialysate inner flow path 1a as the dialysate heating flow path of the first planar panel 1, and the first replacement fluid inner flow path 1b as the replacement fluid heating flow path are in contact with the heater surface of the heating apparatus. Thus, the dialysate and the replacement fluid supplied to the patient side can be heated to and maintained at a predetermined temperature.

In this embodiment, the blood purification apparatus D has, for example, the above-described dialysate feed pump 102, replacement fluid feed pump 103, drainage feed pump 101, dialysate supply blocking valve 112, replacement fluid supply blocking valve 113, and drainage blocking valve 111, and the like, in addition to the scale 154 and the heating apparatus.

The operation of measuring the amount of water removed in CHDF will be described below. In the first phase, the drainage blocking valve 111 is opened, the air valve 116 is closed, and the air pump 117 is stopped. The drainage fed by the feed pump 101 is discarded through the drainage flow path 13. The dialysate supply blocking valve 112 and the replacement fluid supply blocking valve 113 are opened to store the dialysate in the dialysate storage container 9 in the center of the second planar panel 2 and store the replacement fluid in the replacement fluid storage container 10 on the right side of the second planar panel 2. In the second phase, the drainage blocking valve 111 is closed, and the air valve 116 is opened. The drainage fed by the feed pump 101 is stored in the drainage storage container 8 on the left side of the second planar panel 2. On the other hand, the dialysate supply blocking valve 112 and the replacement fluid supply blocking valve 113 are closed. The dialysate and the replacement fluid are supplied from the storage containers in the center and on the right side of the second planar panel 2. Therefore, by measuring weight during this, the amount of water removed is directly measured, and high-precision water removal control is possible.

The drainage blocking valve 111, the dialysate supply blocking valve 112, and the replacement fluid supply blocking valves 113 and 114 should have the function of closing and opening the flow path, for example, a pinch valve which closes the flow path by mechanically pinching the soft tube forming the flow path and opens the flow path by releasing pinching. The mechanically pinching site is moved by a drive source, such as a translation solenoid and a rotary solenoid, to close or open the soft tube.

In the above example, the case of CHDF has been shown, but when the flow rate of the dialysate feed pump is 0, the system performs CHF, and when the flow rate of the replacement fluid feed pump is 0, the system functions as CHD.

Also, in the above example, the replacement fluid supplying tubing part C3 is connected to the blood returning tubing part 82, but the replacement fluid supplying tubing part C3 may be connected to the blood drawing tubing part 81.

The flow paths 14, 15, 33, 34, and 53 connecting the first planar panel 1 and the second planar panel 2 are soft tubes, and the shape and material of the soft tubes themselves, and the spatial location of the soft tubes are selected to satisfy the following conditions.

For example, description is given using FIG. 23. The weight of the second planar panel 2 is measured by the scale 154 when the first planar panel 1 is fixed at a predetermined position, the second planar panel 2 is fixed to the scale 154 of the blood purification apparatus D, and the three storage containers 8, 9, and 10 in the second planar panel are all empty. This weight is a weight B (FIG. 23 (A)). Next, when a liquid having a weight W is placed only in the drainage storage container 8, the weight is measured by the scale 154, and the value obtained by subtracting from the resultant weight the weight B is a weight Wf (FIG. 23 (B)). Similarly, the value obtained by subtracting the weight B from the weight of the second planar panel 2, with a liquid having the weight W placed only in the dialysate storage container 9, is a weight Wd (FIG. 23 (C)), and the value obtained by subtracting the weight B from the weight of the second planar panel 2, with a liquid having the weight W placed only in the replacement fluid storage container 10, is a weight Wr (FIG. 23 (D)). Then, for example, the soft tubes 14, 15, 33, 34, and 53 connecting the first planar panel 1 and the second planar panel 2 are located to satisfy the following formulas (1) and (2).

$$|Wf-Wr|/W \leq 0.005 \quad (1)$$

$$|Wf-Wd|/W \leq 0.005 \quad (2)$$

The weight Wf, Wd, and Wr fluctuate depending on the spatial location of the soft tubes.

In this case, the effect of the invention in this application is obtained that the error of the amount of water removed is reduced to about 0.5% of the amount of the drainage drained by the drainage feed pump, so that the amount of water removed can be controlled with precision four times higher than conventional one. Also, disturbance, such as vibration applied to the first planar panel 1 by the feed pumps 101, 102, and 103, and the blocking valves 111, 112, and 113, and disturbance propagating from the drainage flow paths 12 and 13, the dialysate flow paths 32 and 35, and the replacement fluid flow paths 52 and 54 to the first planar panel 1 do not easily propagate to the second planar panel 2, so that stable and accurate measurement can be performed.

Figure 24:
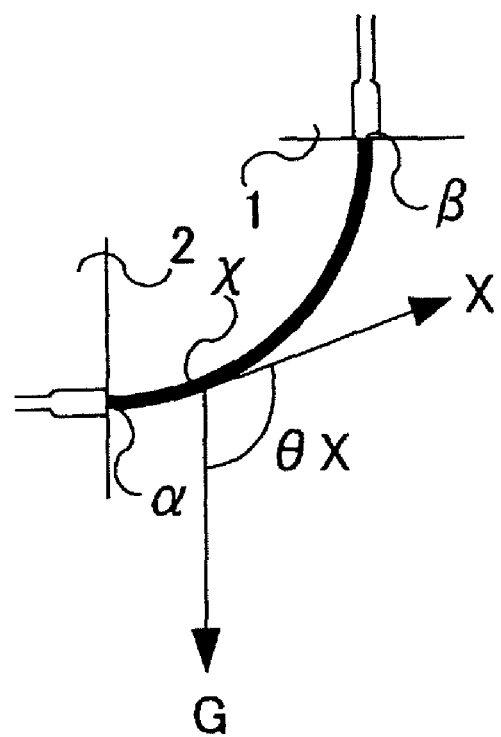
FIG. 24 is a schematic view explaining a vector G, a vector X, and an angle θX.

The location of the soft tubes should be appropriately adjusted to satisfy the formulas (1) and (2), and the soft tubes are more preferably located as follows. Description is given using FIG. 24. For example, one end side of the soft tube is connected at an end α on the second planar panel 2, the other end side is connected at an end β on the first planar panel 1, and the soft tube is located so that when the axial direction (tangential direction) in an arbitrary portion χ in the longitudinal direction of the soft tube connecting the end α and the end β is a vector X, the gravity direction in the arbitrary portion χ is a vector G, and the narrower angle formed by the vector X and the vector G is an angle θX, at least one portion χ in which the angle θX is 70° to 110° is present. The angle θX is the narrower angle, 180° or less, of angles formed by the vector X and the vector G.

Figure 2:
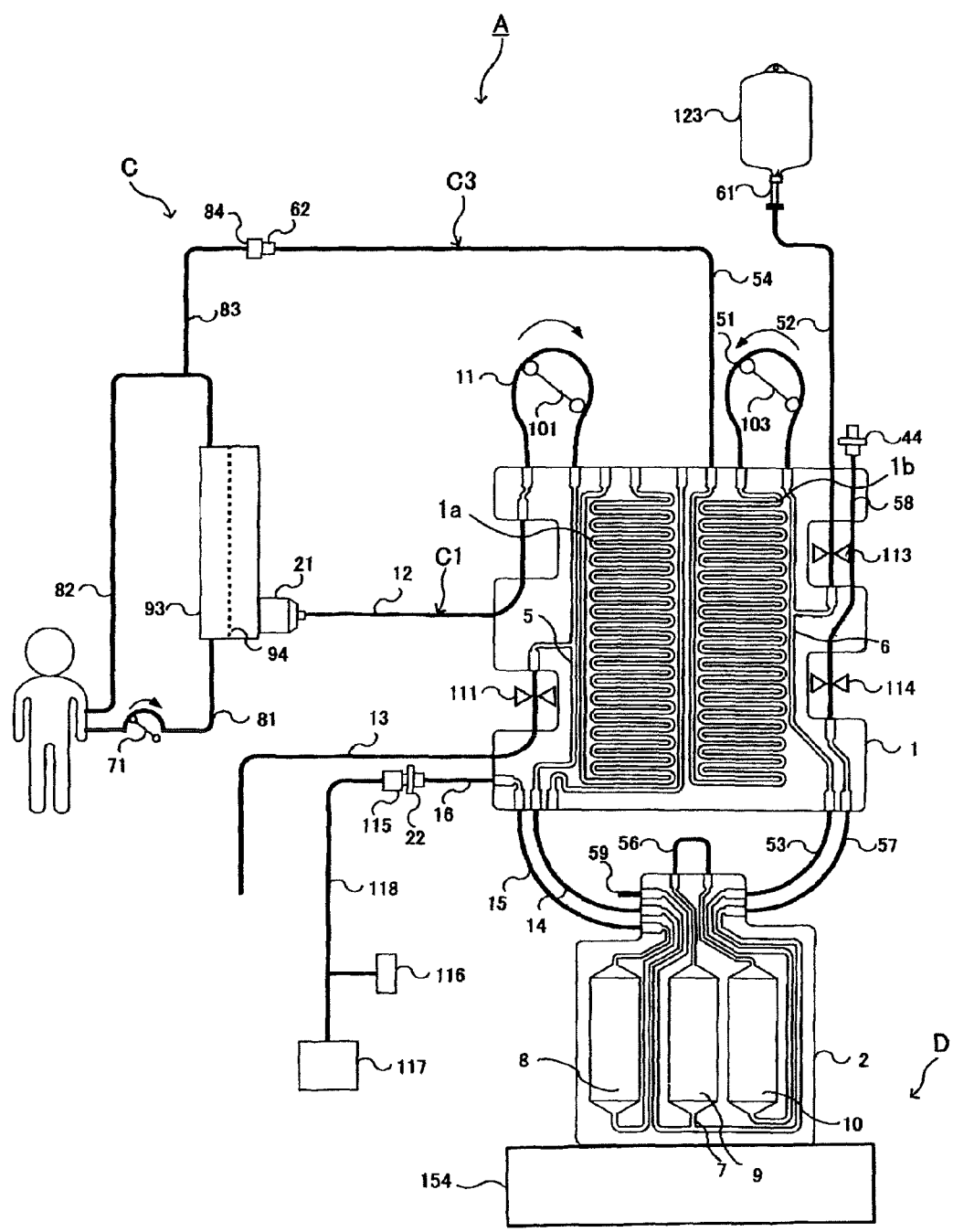
FIG. 2 is a schematic view showing another embodiment of the blood purification system according to the present invention.
Figure 4:
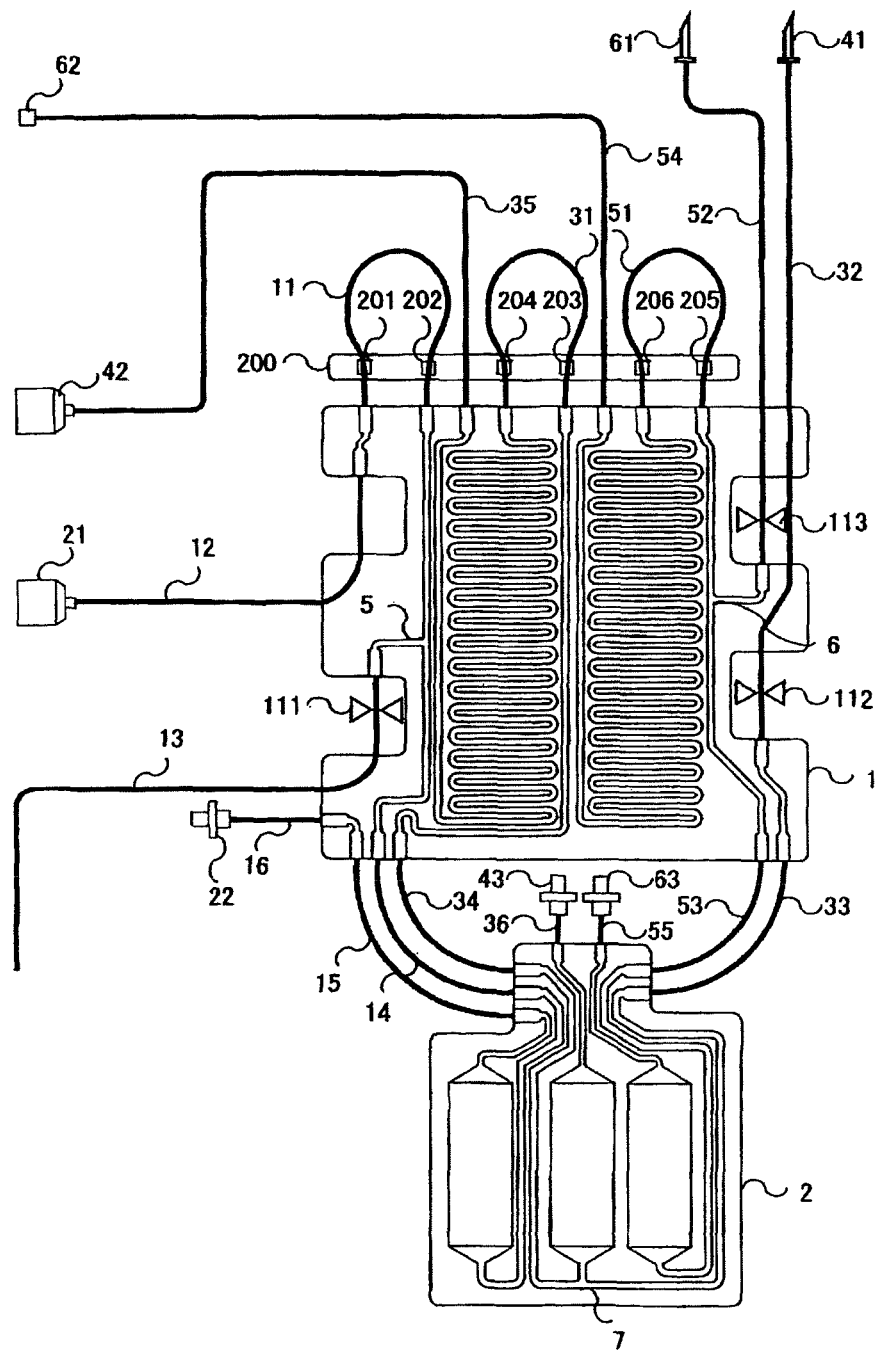
FIG. 4 is a schematic view showing another embodiment of the blood purification system according to the present invention.

In examples in FIGS. 1, 2, and 4, the soft tube is bent at a generally right angle into an L-shape and connected, but the soft tube may be bent at 180° into a U-shape. When the angle formed by the soft tube is a generally right angle, the soft tube can be short, which is economical, therefore, such an angle is most preferred. Also, a soft tube of any material and shape (length, diameter, and thickness) can be used as long as the formulas (1) and (2) are satisfied.

Embodiments of the soft tubes spanning the first planar panel 1 and the second planar panel 2 are shown in FIG. 5 to FIG. 10, and FIG. 11 to FIG. 20.

Figure 5:
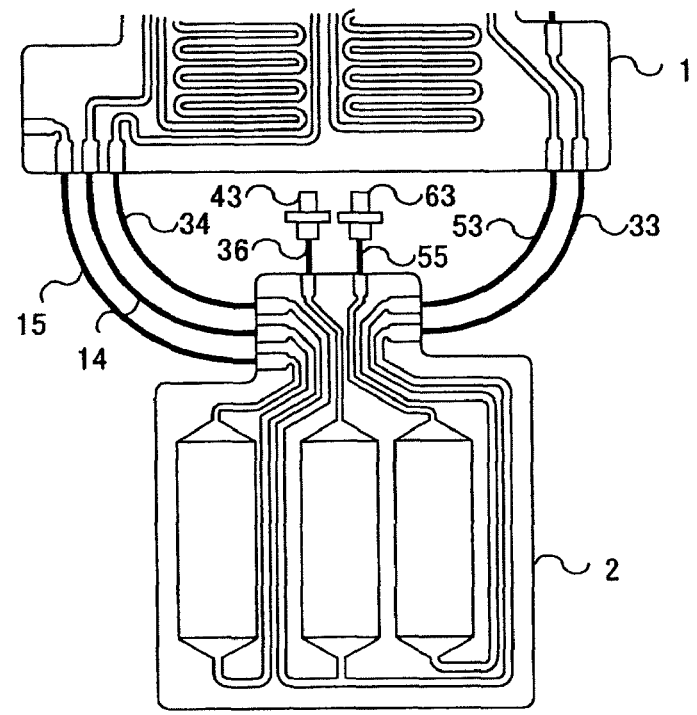
FIG. 5 is a schematic view showing an example of the location of the flow paths spanning the first planar panel and the second planar panel in the blood purification system according to the present invention.

FIG. 5 is an example in which the soft tubes of the drainage flow paths 14 and 15, the dialysate flow paths 33 and 34, and the replacement fluid flow path 53 are connected, bent at a generally right angle, and the angle θX formed by the vector X and the vector G in the vicinity of the connection part between the soft tube and the second planar panel 2 is generally 90°.

Figure 6:
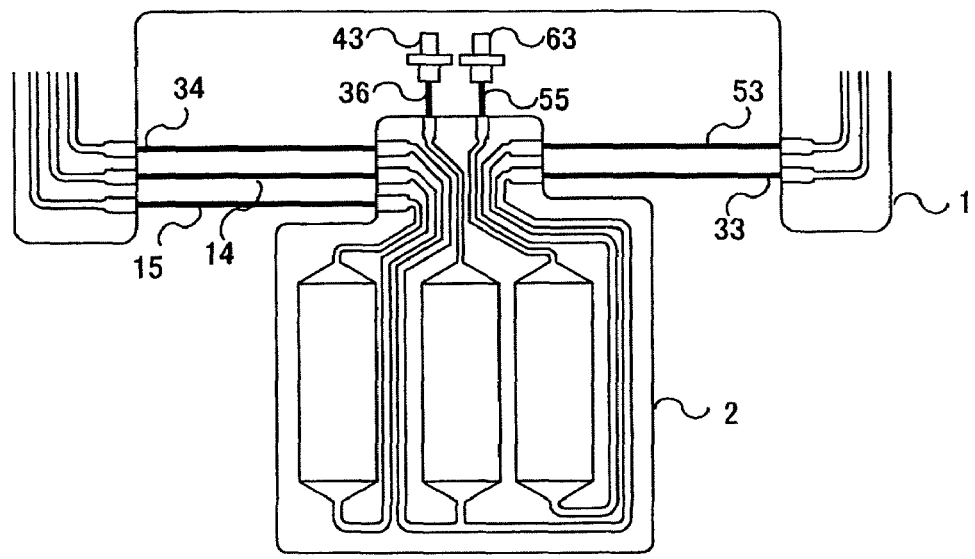
FIG. 6 is a schematic view showing another example of the location of the flow paths spanning the first planar panel and the second planar panel in the blood purification system according to the present invention.

FIG. 6 is an example in which the soft tubes of the drainage flow paths 14 and 15, the dialysate flow paths 33 and 34, and the replacement fluid flow path 53 are horizontally connected, and the angle θX formed by the vector X and the vector G at all sites of the soft tube is generally 90°.

Figure 7:
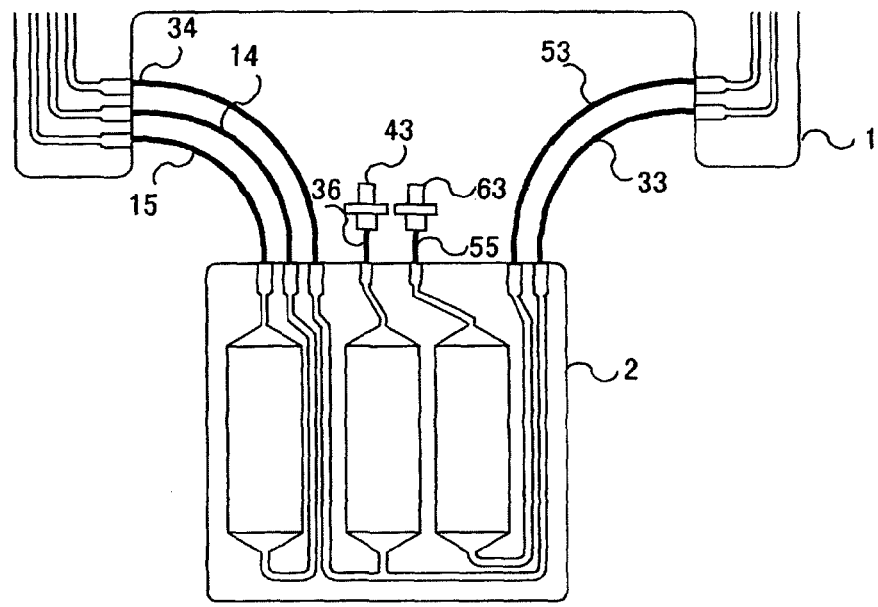
FIG. 7 is a schematic view showing another example of the location of the flow paths spanning the first planar panel and the second planar panel in the blood purification system according to the present invention.

FIG. 7 is another example in which the soft tubes of the drainage flow paths 14 and 15, the dialysate flow paths 33 and 34, and the replacement fluid flow path 53 are connected, bent at a generally right angle, and the angle θX formed by the vector X and the vector G in the vicinity of the connection part between the soft tube and the first planar panel 1 is generally 90°.

Figure 8:
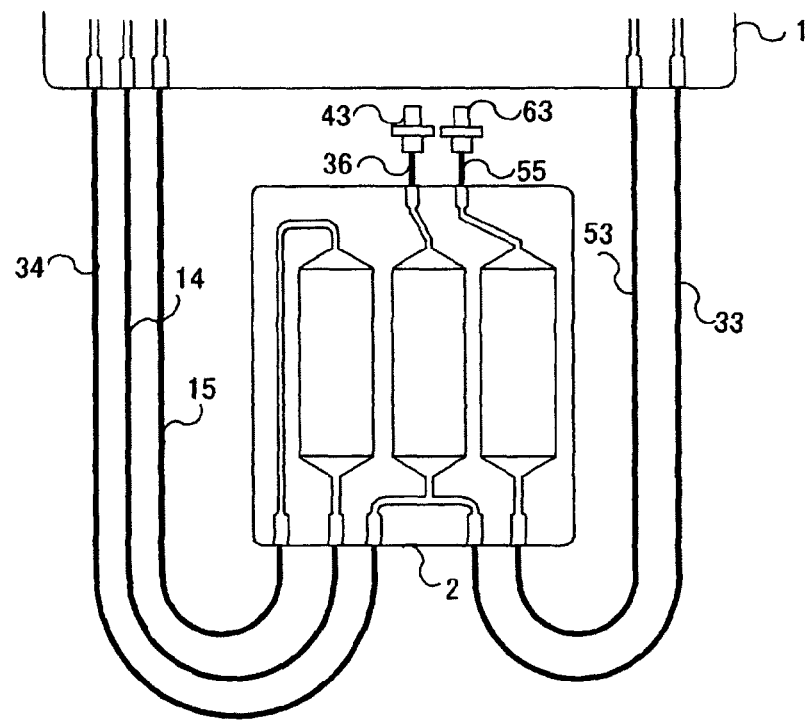
FIG. 8 is a schematic view showing another example of the location of the flow paths spanning the first planar panel and the second planar panel in the blood purification system according to the present invention.

FIG. 8 is an example in which the soft tubes of the drainage flow paths 14 and 15, the dialysate flow paths 33 and 34, and the replacement fluid flow path 53 are connected, bent in a U-shape, and the angle θX formed by the vector X and the vector G in the bottom portion of the U-shape is generally 90°.

Figure 9A:
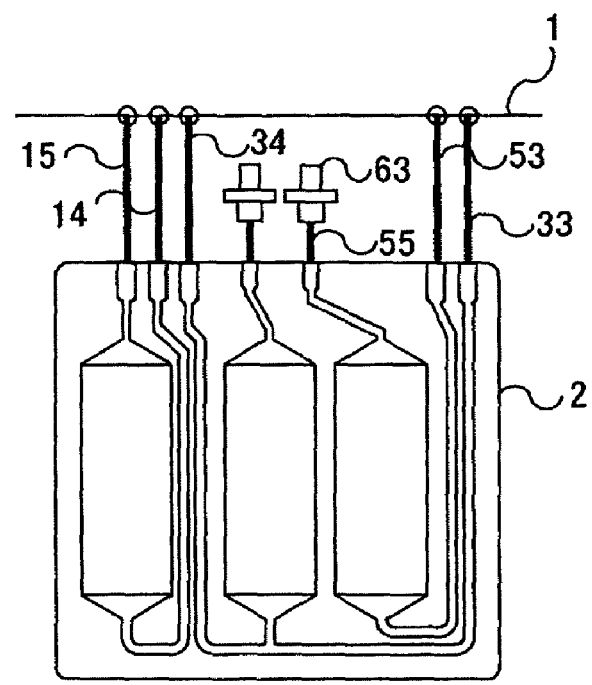
FIG. 9(A) is a front view.
Figure 9B:
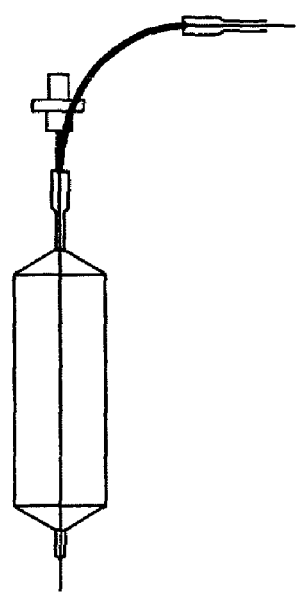
FIG. 9(B) is a side view.

FIG. 9 is another example in which the soft tubes of the drainage flow paths 14 and 15, the dialysate flow paths 33 and 34, and the replacement fluid flow path 53 are connected, bent at a generally right angle. The soft tubes of the drainage flow paths 14 and 15, the dialysate flow paths 33 and 34, and the replacement fluid flow path 53 are linearly connected when viewed from the front (FIG. 9 (A)), but the soft tubes of the drainage flow paths 14 and 15, the dialysate flow paths 33 and 34, and the replacement fluid flow path 53 are connected, bent at a generally right angle, when viewed from a side (FIG. 9 (B)), and the angle θX formed by the vector X and the vector G in the vicinity of the connection part between the soft tube and the first planar panel is generally 90°.

Figure 10:
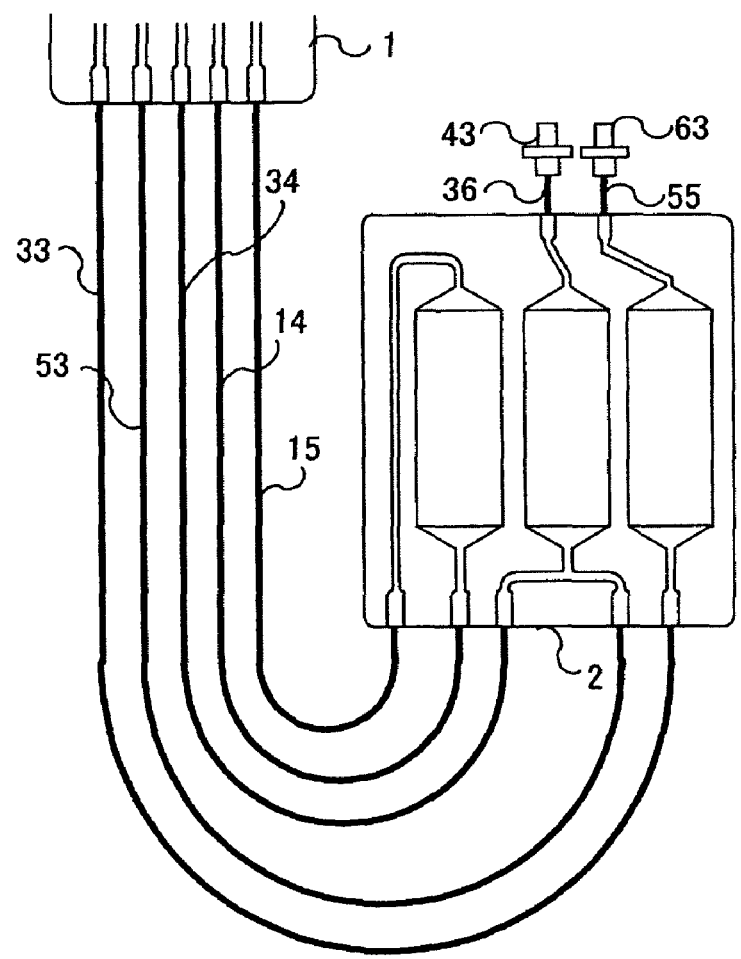
FIG. 10 is a schematic view showing another example of the location of the flow paths spanning the first planar panel and the second planar panel in the blood purification system according to the present invention.

FIG. 10 is another example in which the soft tubes of the drainage flow paths 14 and 15, the dialysate flow paths 33 and 34, and the replacement fluid flow path 53 are connected, bent in a U-shape. The soft tubes of the drainage flow paths 14 and 15, the dialysate flow paths 33 and 34, and the replacement fluid flow path 53 are connected, bent in the same direction, and the angle θX formed by the vector X and the vector G in the bottom portion of the U-shape is generally 90°.

FIG. 11 to FIG. 20 illustrate one of the flow paths connecting the first planar panel 1 and the second planar panel 2.

Figure 11:
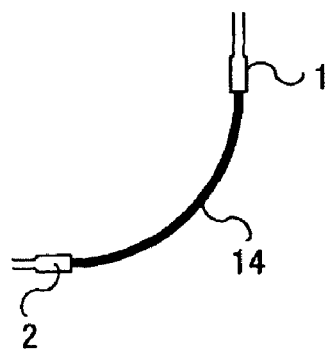
FIG. 11 is a schematic view showing an example of the location of the flow paths spanning the first planar panel and the second planar panel in the blood purification system according to the present invention, in which one of the flow paths is selected and illustrated.

FIG. 11 is an example in which the soft tube of one flow path (for example, the drainage flow path 14) providing communication between both the first planar panel 1 and the second planar panel 2 is connected at a generally right angle, and the angle θX formed by the vector X and the vector G in the vicinity of the connection part between the soft tube and the second planar panel 2 is generally 90°.

Figure 12:
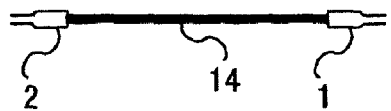
FIG. 12 is a schematic view showing another example of the location of one flow path spanning the first planar panel and the second planar panel in the blood purification system according to the present invention.

FIG. 12 is an example in which the soft tube of one flow path (for example, the drainage flow path 14) providing communication between both the first planar panel 1 and the second planar panel 2 is horizontally connected, and the angle θX formed by the vector X and the vector G at all sites of the soft tube is generally 90°.

Figure 13:
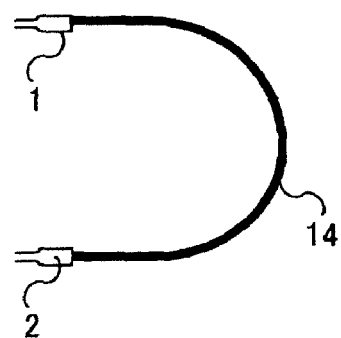
FIG. 13 is a schematic view showing another example of the location of one flow path spanning the first planar panel and the second planar panel in the blood purification system according to the present invention.

FIG. 13 is an example in which the soft tube of one flow path (for example, the drainage flow path 14) providing communication between both the first planar panel 1 and the second planar panel 2 is connected in a U-shape rotated counterclockwise generally 90°, and the angle θX formed by the vector X and the vector G in the vicinity of the connection part between the soft tube and the first planar panel 1 is generally 90° and in the vicinity of the connection part between the soft tube and the second planar panel 2 is generally 90°.

Figure 14:
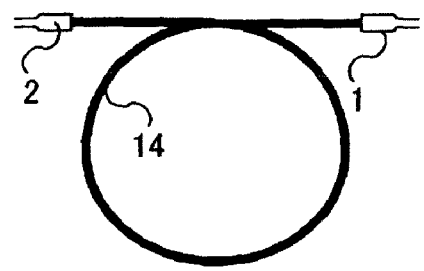
FIG. 14 is a schematic view showing another example of the location of one flow path spanning the first planar panel and the second planar panel in the blood purification system according to the present invention.

FIG. 14 is an example in which the soft tube of one flow path (for example, the drainage flow path 14) providing communication between both the first planar panel 1 and the second planar panel 2 is horizontally connected, and is connected, bent to form a loop, and the angle θX formed by the vector X and the vector G in the horizontal portion of the soft tube and the bottom portion of the loop is generally 90°.

Figure 15:
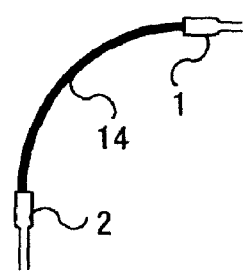
FIG. 15 is a schematic view showing another example of the location of one flow path spanning the first planar panel and the second planar panel in the blood purification system according to the present invention.

FIG. 15 is another example in which the soft tube of one flow path (for example, the drainage flow path 14) providing communication between both the first planar panel 1 and the second planar panel 2 is connected at a generally right angle, and the angle θX formed by the vector X and the vector G in the vicinity of the connection part between the soft tube and the first planar panel 1 is generally 90°.

Figure 16:
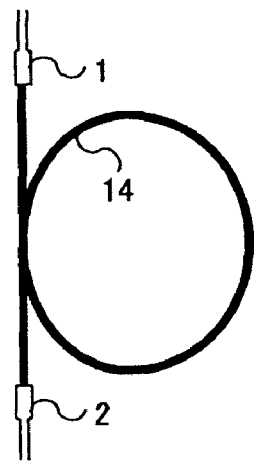
FIG. 16 is a schematic view showing another example of the location of one flow path spanning the first planar panel and the second planar panel in the blood purification system according to the present invention.

FIG. 16 is another example in which the soft tube of one flow path (for example, the drainage flow path 14) providing communication between both the first planar panel 1 and the second planar panel 2 is vertically connected, and is connected, bent to form a loop, and the angle θX formed by the vector X and the vector G in the upper part and lower part of the loop is generally 90°.

Figure 17:
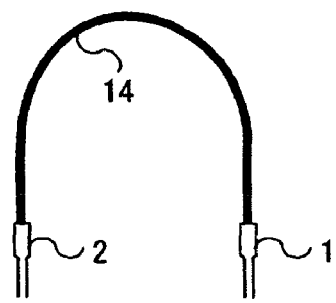
FIG. 17 is a schematic view showing another example of the location of one flow path spanning the first planar panel and the second planar panel in the blood purification system according to the present invention.

FIG. 17 is another example in which the soft tube of one flow path (for example, the drainage flow path 14) providing communication between both the first planar panel 1 and the second planar panel 2 is connected, bent in an inverted U-shape, and the angle θX formed by the vector X and the vector G in the upper part of the inverted U-shape is generally 90°.

Figure 18:
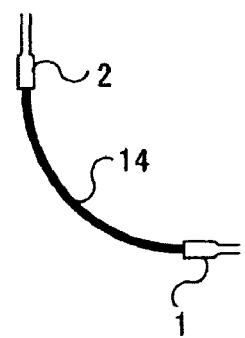
FIG. 18 is a schematic view showing another example of the location of one flow path spanning the first planar panel and the second planar panel in the blood purification system according to the present invention.

FIG. 18 is another example in which the soft tube of one flow path (for example, the drainage flow path 14) providing communication between both the first planar panel 1 and the second planar panel 2 is connected at a generally right angle, and the angle θX formed by the vector X and the vector G in the vicinity of the connection part between the soft tube and the first planar panel 1 is generally 90°.

Figure 19:
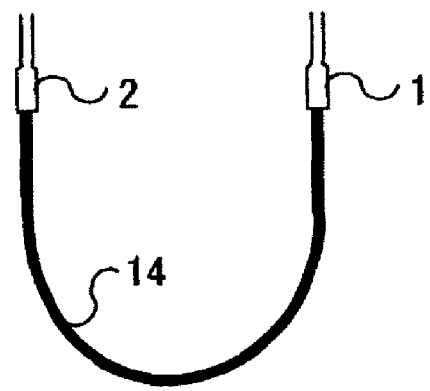
FIG. 19 is a schematic view showing another example of the location of one flow path spanning the first planar panel and the second planar panel in the blood purification system according to the present invention.

FIG. 19 is an example in which the soft tube of one flow path (for example, the drainage flow path 14) providing communication between both the first planar panel 1 and the second planar panel 2 is connected, bent in a U-shape, and the angle θX formed by the vector X and the vector G in the lower part of the U-shape is generally 90°.

Figure 20:
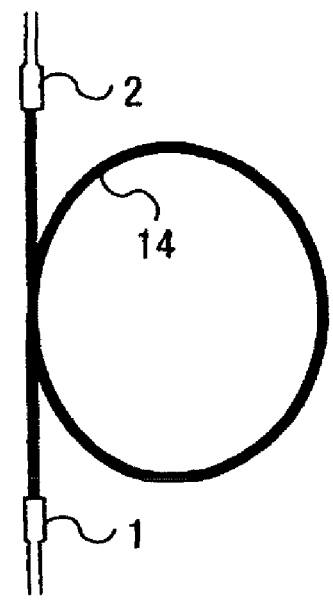
FIG. 20 is a schematic view showing another example of the location of one flow path spanning the first planar panel and the second planar panel in the blood purification system according to the present invention.

FIG. 20 is another example in which the soft tube of one flow path (for example, the drainage flow path 14) providing communication between both the first planar panel 1 and the second planar panel 2 is vertically connected, and is connected, bent to form a loop, and the angle θX formed by the vector X and the vector G in the upper part and lower part of the loop is generally 90°.

Figure 21:
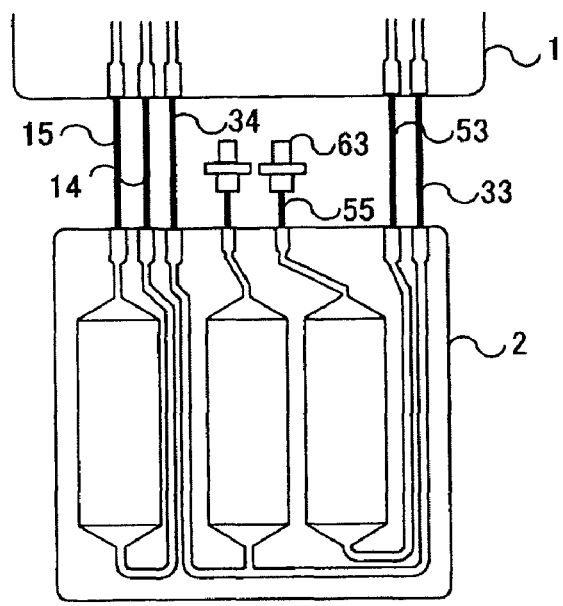
FIG. 21 is a schematic view showing one example of the flow paths spanning the first planar panel and the second planar panel, not included in the present invention.
Figure 22:
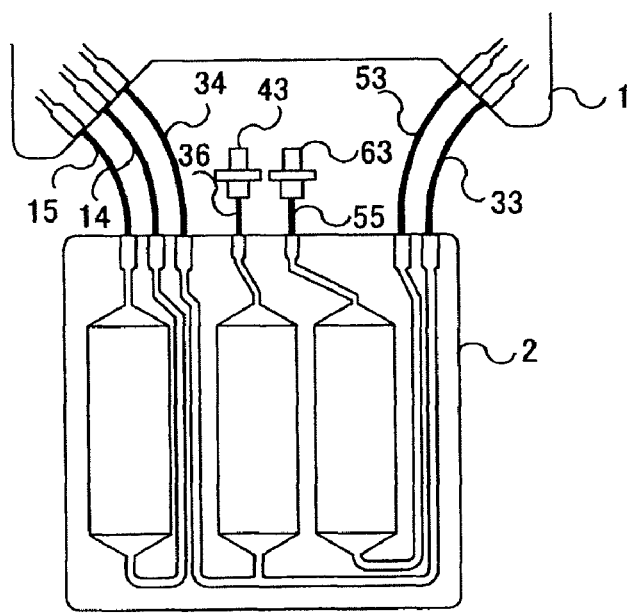
FIG. 22 is a schematic view showing another example of the flow paths spanning the first planar panel and the second planar panel, not included in the present invention.
Figure 23A:
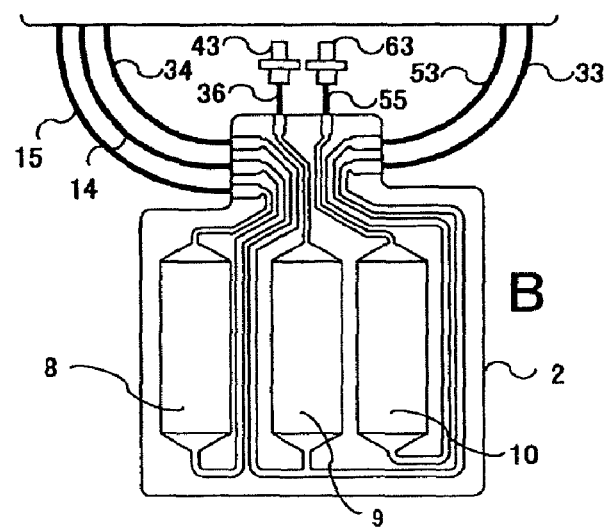
FIG. 23 is a schematic view showing an outline in which the weight of the second planar panel is measured with a liquid having a weight W placed in three storage containers; (A) shows that the weight of the second planar panel when three storage containers are all empty is B, (B) shows that the weight of the second planar panel when a liquid having a weight W is placed only in the drainage storage container is Wf+B, (C) shows that the weight of the second planar panel when a liquid having the weight W is placed only in the dialysate storage container is Wd+B, and (D) shows that the weight of the second planar panel when a liquid having the weight W is placed only in the replacement fluid storage container is Wr+B.
Figure 23B:
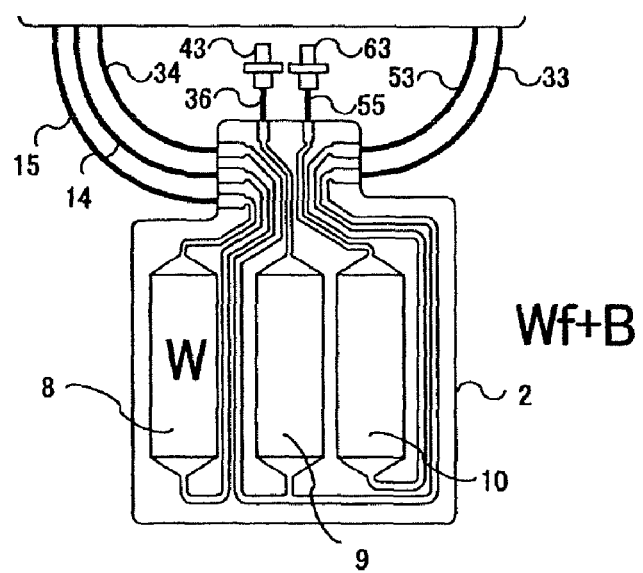
Figure 23C:
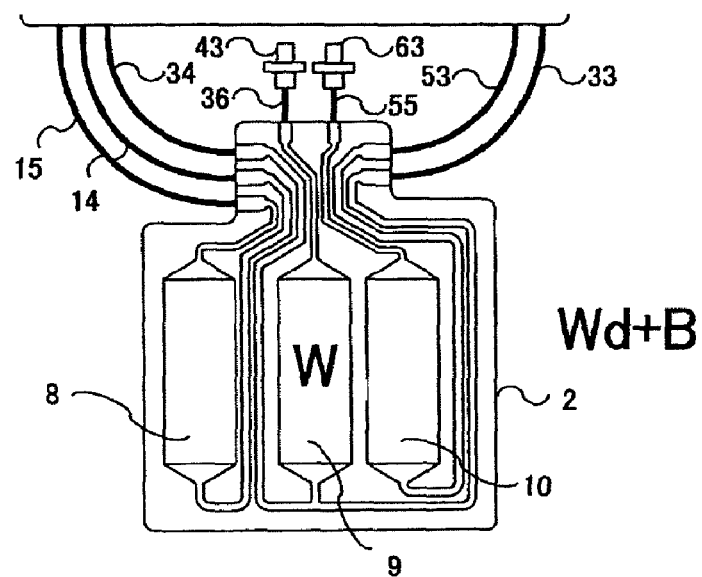
Figure 23D:
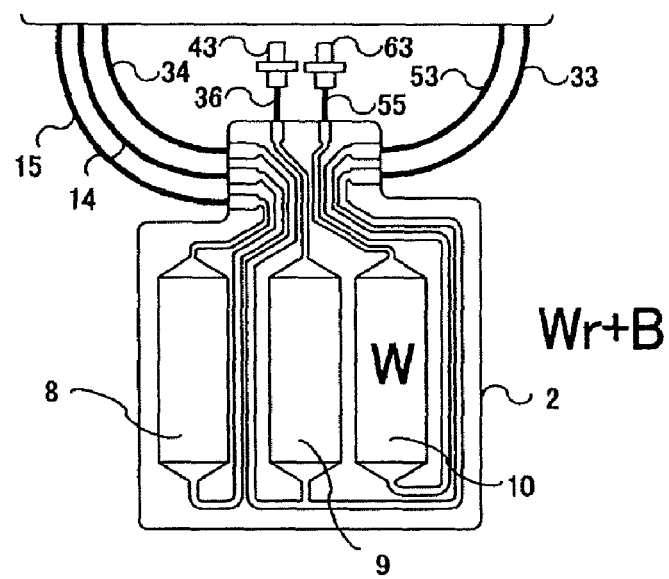

The embodiments regarding the location of the soft tubes spanning the first planar panel 1 and the second planar panel 2 are illustrated in FIG. 5 to FIG. 20, as described above. On the other hand, the location of the soft tubes spanning the first planar panel 1 and the second planar panel 2, not included in the present invention, is illustrated in FIG. 21 and FIG. 22. In examples in FIG. 21 and FIG. 22, the angle θX formed by the vector X and the vector G is not 70° to 110° in any portion of the soft tubes spanning the first planar panel 1 and the second planar panel 2.

In the above embodiments, examples of the location of the soft tubes that satisfies the above formulas (1) and (2) have been described, but the material and shape, such as length, of the soft tubes may be selected to satisfy the formulas (1) and (2). Also, both the location of the soft tubes, and the material, shape, and the like of the soft tubes may be set to satisfy the formulas (1) and (2).

FIG. 2 shows one embodiment of another blood purification system A according to the present invention. This system A shows plasma exchange PE. In PE, a membrane type plasma separator 93, as a blood purifier, housing a plasma separation membrane 94 is used, and a plasma component is drained through the plasma separation membrane 94, while fresh frozen plasma or an albumin solution is supplied into the body.

A first planar panel 1 and a second planar panel 2 are identical to the panels shown in FIG. 1, and tubings connected to the first planar panel 1 and the second planar panel 2 are changed.

Plasma separated from the membrane type plasma separator 93 is fed by a drainage feed pump 101, and discarded through a drainage flow path 12, the first planar panel 1, a pump tube 11, the first planar panel 1, and a drainage flow path 13. A branch is present inside the first planar panel 1, and the drainage branch duct 5 is connected to a drainage flow path 14. The drainage flow path 14 is connected to the second planar panel 2, and connected to a drainage flow path 15, the first planar panel 1, and a drainage flow path 16 in the order. A transducer protection filter 22 is connected to the end of the drainage flow path 16. The transducer protection filter 22 is connected to a connection part 115. The connection part 115 is connected to a tubing 118. The tubing 118 branches off, and one is connected to an air valve 116. The other branching tubing is connected to an air pump 117. Also, a drainage main duct inside the first planar panel 1 is connected to the drainage flow path 13 having its end open, and a drainage blocking valve (part) 111 is provided in the drainage flow path 13.

A replacement fluid bag (replacement fluid storage part) 123 storing fresh frozen plasma or an albumin solution is connected to a replacement fluid flow path 52 via a plastic needle 61. The replacement fluid flow path 52 is connected to the first planar panel 1. A branch is present inside the first planar panel 1, and a replacement fluid main duct is connected to the branch flow path 83 of a blood returning tubing through a replacement fluid feed pump tube 51, the first planar panel 1, and a replacement fluid flow path 54. A replacement fluid branch duct 6 branching off in the first planar panel 1 is connected to a replacement fluid flow path 53, and connected to the replacement fluid storage container 10 of the second planar panel 2, a coupling tube 56, another container 9 of the second planar panel 2 (in the above embodiment, the dialysate storage container 9), a replacement fluid flow path 57 connecting the second planar panel 2 and the first planar panel 1, the first planar panel 1, and a flow path 58 in the order. A transducer protection filter 44 is connected to the end of the flow path 58. One branching off in the lower part of another container 9 in the center of the first planar panel 2 is closed in a closure part 59. Also, replacement fluid supply blocking valves (parts) 113 and 114 are provided in the replacement fluid flow path 52 and the flow path 58.

The soft tubes of the drainage flow paths 14 and 15 and the replacement fluid flow paths 53 and 57 connecting the first planar panel 1 and the second planar panel 2 are selected to satisfy the above formula (1). In other words, the soft tubes and the location of the soft tubes are selected to satisfy the following formula (1) when the weight of the second planar panel 2, with the drainage storage container 8, the replacement fluid storage container 10, and another container 9 being empty, is B, the value obtained by subtracting the weight B from the weight of the second planar panel 2, with a liquid having a weight W placed only in the drainage storage container 8, is Wf, and the value obtained by subtracting the weight B from the weight of the second planar panel 2, with a liquid having the weight W placed only in the replacement fluid storage container 10, is Wr, and when each weight of B, Wf, and Wr is obtained from a numerical value measured by the scale 154 of a blood purification apparatus D.

$$|Wf - Wr|/W \leq 0.005 \tag{1}$$

The method for locating the soft tubes to satisfy the above condition, and the like are similar to those in the above-described embodiment.

The second planar panel 2 is fixed and held on the scale 154 and measured.

The operation of measuring the amount of drainage and the amount of replacement in PE will be described below. In the first phase, the drainage blocking valve 111 is opened, the air valve 116 is closed, and the air pump 117 is stopped. Plasma fed by the drainage feed pump 101 is discarded through the drainage flow path 13. In the second phase, the drainage blocking valve 111 is closed, the air valve 116 is opened to the air, and the air pump 117 is stopped. The plasma fed by the drainage feed pump 101 is stored in the drainage storage container 8 on the left side of the second planar panel 2 through the drainage flow path 14. By measuring weight during this, the flow rate of the drainage feed pump 101 is measured. In the third phase, the blocking valve 111 is opened, the air valve 116 is closed, and the air pump 117 is operated. Air fed by the air pump 117 passes through a tubing 118, and is fed to the drainage storage container 8 on the left side of the second planar panel 2 through the drainage flow paths 16 and 15, and the plasma stored in the drainage storage container 8 is discarded through the drainage flow path 14, the first planar panel 1, and the drainage flow path 13. Also, the plasma fed by the drainage feed pump 101 is simultaneously discarded through the drainage flow path 13. Returning to the first phase again, a series of operations are repeated.

On the other hand, similar operations are also performed on the replacement fluid side to measure the flow rate of the replacement fluid. While the drainage side is in the first phase, the following operations are performed on the replacement fluid side. In the first phase, the replacement fluid supply blocking valve 113 is opened, and the replacement fluid supply blocking valve 114 is also opened. A predetermined amount of the replacement fluid is stored in the replacement fluid storage container 10 on the right side of the second planar panel 2 through the replacement fluid flow path 52, the first planar panel 1, and the replacement fluid flow path 53. During this, the replacement fluid feed pump 103 is operated, and the replacement fluid is injected into the blood returning tubing part 82 through the replacement fluid flow path 52, the first planar panel 1, and the replacement fluid flow path 54. In the second phase, the replacement fluid supply blocking valve 113 is opened, and the replacement fluid supply blocking valve 114 is closed. After the second phase, in the third phase, the replacement fluid supply blocking valve 113 is closed, and the replacement fluid supply blocking valve 114 is opened. The replacement fluid stored in the storage container on the right side of the second planar panel 2 is fed by the replacement fluid feed pump 103. By measuring weight during this, the flow rate of the drainage feed pump 101 is measured. Returning to the first phase again, a series of operations are repeated.

When the drainage side is in the first phase, a series of measurement operations are performed on the replacement fluid side. When the replacement fluid side reaches the second phase again, measurement operations on the drainage side are performed. On measurement results, feedback control for the correction of the flow rate of respective feed pumps 101 and 103 is performed.

In the above example, another container 9 serves as a flow path that simply passes air. Also, another container 9 may be used as a dialysate storage container in the case of CHDF. Also, in the above example, the second planar panel 2 may be devoid of another container 9. In such a case, the weight B in the formula (1) may be the weight of the second planar panel 2, with the drainage storage container 8 and the replacement fluid storage container 10 being empty. Further, in the above example, the first planar panel 1 and the second planar panel 2 having the same configuration as in the above embodiment with the dialysate supplying tubing part C1 are used, but a first planar panel and a second planar panel without a function for dialysate supply may be used.

Figure 3:
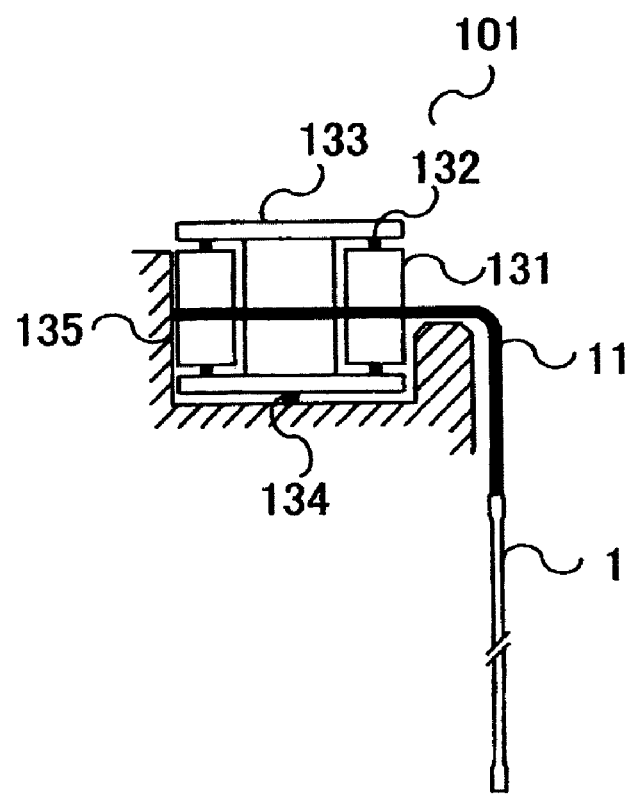
FIG. 3 is a schematic view showing the relative position of the feed pump and the planar panel in the blood purification system according to the present invention.

FIG. 3 shows one embodiment in which disturbance generated by the feed pumps 101, 102, and 103 does not easily propagate to the first planar panel 1, and is a layout of the drainage feed pump 101 as viewed sideways. The drainage feed pump 101 is a rotary tube pump, comprises the elastic tube 11 forming the feed path, and a rotor 133 having a plurality of rollers 131 attached to its outer peripheral part, and has a structure in which by the rotor 133 rotating about a rotation axis 134, the plurality of rollers 131 squeeze the tube 11 to perform feed operation. The tube 11 is arcuately restricted by a stator 135, and the center of the arc is the center 134 of the rotor 133. The plurality of rollers 131 revolve, and rotate about a roller rotation axis 132, to squeeze the tube 11 for feeding.

The portions of the tube 11 squeezed by the rollers 131, and the first planar panel 1 are located at a position where the tube 11 is bent at a generally right angle. The tube squeezed by the rollers 131 repeats pressure closing and opening. When pressure closed, the tube 11 moves to the left in the horizontal direction shown in FIG. 3, and when opened, the tube 11 moves to the right in the horizontal direction. The tube 11 causes vibration from side to side by being squeezed by the rollers 131. To make it difficult to propagate this vibration in the horizontal direction to the first planar panel 1, the tube 11 is bent at a generally right angle. The tube 11 made of a soft material absorbs this vibration in the horizontal direction, so that vibration in the vertical direction can be suppressed.

FIG. 4 is a schematic view in which a part 201 on the inlet side and a part 202 on the outlet side of the drainage feed pump tube 11, a part 203 on the inlet side and a part 204 on the outlet side of the dialysate feed pump tube 31, and a part 205 on the inlet side and a part 206 on the outlet side of the replacement fluid feed pump tube 51 are fixed by a fixture 200. The fixture 200 has recesses, and the tubes are fit and fixed in the recesses. As the material of the fixture, synthetic resins, particularly thermoplastic resins, are preferred in terms of manufacturing cost, processability, and operability. As the thermoplastic resins, polyolefin resins, polyamide resins, polyester resins, polyurethane resins, fluorine resins, silicon resins, and the like, and further, ABS (acrylonitrile-butadiene-styrene copolymer) resins, polyvinyl chloride, polycarbonate, polystyrene, polyacrylate, polyacetal, and the like can be illustrated. Any of them can be preferably used.

By providing the fixture 200, the shape of the pump tubes 11, 31, and 51 is stabilized, and the operability of mounting the pump tubes in the feed pumps 101, 102, and 103 is easier.

The membrane type plasma separator is one in which a housing is loaded with a hollow fiber type separation membrane having a pore diameter not passing at least blood cells. When blood is flowed inside the hollow fiber, the plasma component is separated through the hollow fiber membrane wall. The material of the separation membrane is not particularly limited, and for example, polysulfone, polyethersulfone, polyethylene, polypropylene, cellulose acetate, ethylene vinyl alcohol, polyacrylonitrile, polyethylene fluoride, polyester, and the like can be illustrated.

The blood purifier is one in which a housing is loaded with a hollow fiber type semipermeable membrane passing small molecules, such as urea nitrogen, creatinine, and uric acid, and low molecular weight protein smaller than or equal to albumin in blood. When blood is flowed inside the hollow fiber, small molecules and low molecular protein are separated through the hollow fiber membrane wall. The material of the separation membrane is not particularly limited, and for example, polysulfone, polyethersulfone, polyethylene, polypropylene, cellulose, cellulose acetate, ethylene vinyl alcohol, polyacrylonitrile, polyethylene fluoride, polyester, polymethyl methacrylate, and the like can be illustrated.

INDUSTRIAL APPLICABILITY

The blood purification system of the present invention is useful because in performing blood purification, particularly continuous blood purification and plasma exchange, the amount of water removed and the amount of the replacement fluid can be accurately controlled, furthermore, the preparation operation is easy, and improper mounting does not easily occur.

The invention claimed is:

1. A blood purification system comprising a blood purification tubing and a blood purification apparatus, wherein the blood purification tubing has a blood drawing tubing part for feeding blood drawn from a patient to a blood purifier, a blood returning tubing part for returning blood in the blood purifier to the patient, a dialysate supplying tubing part for supplying a dialysate to the blood purifier, a drainage tubing part for performing drainage from the blood purifier, and a replacement fluid supplying tubing part for supplying a replacement fluid to the blood drawing tubing part or the blood returning tubing part, the dialysate supplying tubing part has a dialysate storage container, the drainage tubing part has a drainage storage container, the replacement fluid supplying tubing part has a replacement fluid storage container, the dialysate supplying tubing part, the drainage tubing part, and the replacement fluid supplying tubing part are each located to pass in a first planar panel and in a second planar panel, the dialysate storage container, the drainage storage container, and the replacement fluid storage container are installed in the second planar panel, flow paths connecting the first planar panel and the second planar panel, in the dialysate supplying tubing part, the drainage tubing part, and the replacement fluid supplying tubing part, are composed of a soft tube, the blood purification apparatus has a scale for measuring the second planar panel, and the soft tubes and location of the soft tubes are selected to satisfy the following formulas (1) and (2) when a weight of the second planar panel, with the three storage containers being empty, is B, a value obtained by subtracting the weight B from a weight of the second planar panel, with a liquid having a weight W placed only in the drainage storage container, is Wf, a value obtained by subtracting the weight B from a weight of the second planar panel, with a liquid having the weight W placed only in the dialysate storage container, is Wd, and a value obtained by subtracting the weight B from a weight of the second planar panel, with a liquid having the weight W placed only in the replacement fluid storage container, is Wr, and when each weight of B, Wf, Wd, and Wr is obtained from a numerical value measured by the scale of the blood purification apparatus $$|Wf-Wr|/W \leq 0.005 \qquad (1)$$

$$|Wf-Wd|/W \leq 0.005 \qquad (2).$$

2. The blood purification system according to claim 1, wherein one end side of the soft tube is connected at an end α on the second planar panel, and the other end side is connected at an end β on the first planar panel, and the soft tube is located so that when an axial direction in an arbitrary portion χ in a longitudinal direction of the soft tube connecting the end α and the end β is a vector X, a gravity direction is a vector G, and a narrower angle formed by the vector X and the vector G is an angle θX, at least one portion χ in which the angle θX is 70° to 110° is present, provided that the vector X is a direction from the second planar panel toward the first planar panel.

3. The blood purification system according to claim 1, wherein the blood purification tubing further has a dialysate feed pump tube, a replacement fluid feed pump tube, and a drainage feed pump tube, the blood purification apparatus further has a dialysate feed pump, a replacement fluid feed pump, and a drainage feed pump for squeezing the pump tubes for feeding, in the dialysate supplying tubing part, the dialysate feed pump tube, a dialysate branch duct, and a dialysate supply blocking part are located in this order from a dialysate inlet side of the blood purifier on a tubing having one end side connected to a dialysate inlet of the blood purifier and the other end side connected to a dialysate storage part, and the dialysate storage container is connected to the dialysate branch duct, in the replacement fluid supplying tubing part, the replacement fluid feed pump tube, a replacement fluid branch duct, and a replacement fluid supply blocking part are located in this order from a blood returning tubing part or blood drawing tubing part side on a tubing having one end side connected to the blood returning tubing part or the blood drawing tubing part and the other end side connected to a replacement fluid storage part, and the replacement fluid storage container is connected to the replacement fluid branch duct, in the drainage tubing part, the drainage feed pump tube, a drainage branch duct, and a drainage blocking part are located in this order from a drainage outlet side of the blood purifier on a tubing having one end side connected to a drainage outlet of the blood purifier and the other end side open, and the drainage storage container is connected to the drainage branch duct, the blood purification apparatus further has a dialysate supply blocking valve, a replacement fluid supply blocking valve, and a drainage blocking valve for blocking the blocking parts, a flow path in a portion near the dialysate feed pump tube and between the dialysate inlet of the blood purifier and the dialysate feed pump tube, and a flow path in a portion near the dialysate feed pump tube and between the dialysate feed pump tube and an end connected to the dialysate storage part, in the dialysate supplying tubing part, a flow path in a portion near the replacement fluid feed pump tube and between an end connected to the blood returning tubing part or the blood drawing tubing part and the replacement fluid feed pump tube, and a flow path in a portion near the replacement fluid feed pump tube and between the replacement fluid feed pump tube and an end on the side connected to the replacement fluid storage part, in the replacement fluid supplying tubing part, and a flow path in a portion near the drainage feed pump tube and between the drainage outlet of the blood purifier and the drainage feed pump tube, and a flow path in a portion near the drainage feed pump tube and between the drainage feed pump tube and an open end, in the drainage tubing part are installed in the first planar panel, the dialysate feed pump tube, the replacement fluid feed pump tube, and the drainage feed pump tube are connected to the first planar panel, and the dialysate branch duct, the replacement fluid branch duct, and the drainage branch duct are installed in the first planar panel or the second planar panel.

4. The blood purification system according to claim 3, wherein the blood purification apparatus has a heating apparatus, the flow path in the portion near the dialysate feed pump tube and between the dialysate inlet of the blood purifier and the dialysate feed pump tube in the dialysate supplying tubing part, installed in the first planar panel, is a dialysate heating flow path, the flow path in the portion near the replacement fluid feed pump tube and between the end connected to the blood returning tubing part or the blood drawing tubing part and the replacement fluid feed pump tube in the replacement fluid supplying tubing part, installed in the first planar panel, is a replacement fluid heating flow path, and at least one surface of the dialysate heating flow path and the replacement fluid heating flow path is in contact with a heater surface of the heating apparatus.

5. The blood purification system according to claim 3, wherein the dialysate feed pump, the replacement fluid feed pump, and the drainage feed pump are tubing pumps, and a plane of an orbit in which a roller revolves, and a planar part of the first planar panel are located at a generally right angle.

6. The blood purification system according to claim 3, wherein having a fixture for fixing a part on an inlet side and/or outlet side of any of the dialysate feed pump tube, the replacement fluid feed pump tube, and the drainage feed pump tube.

7. A blood purification system comprising a blood purification tubing and a blood purification apparatus, wherein the blood purification tubing has a blood drawing tubing part for feeding blood drawn from a patient to a blood purifier, a blood returning tubing part for returning blood in the blood purifier to the patient, a drainage tubing part for performing drainage from the blood purifier, and a replacement fluid supplying tubing part for supplying a replacement fluid to the blood drawing tubing part or the blood returning tubing part, the drainage tubing part has a drainage storage container, the replacement fluid supplying tubing part has a replacement fluid storage container, the drainage tubing part and the replacement fluid supplying tubing part are each located to pass in a first planar panel and in a second planar panel, the drainage storage container and the replacement fluid storage container are installed in the second planar panel, flow paths connecting the first planar panel and the second planar panel, in the drainage tubing part and the replacement fluid supplying tubing part, are composed of a soft tube, the blood purification apparatus has a scale for measuring the second planar panel, and the soft tubes and location of the soft tubes are selected to satisfy the following formula (1) when a weight of the second planar panel, with the drainage storage container and the replacement fluid storage container being empty, is B, a value obtained by subtracting the weight B from a weight of the second planar panel, with a liquid having a weight W placed only in the drainage storage container, is Wf, and a value obtained by subtracting the weight B from a weight of the second planar panel, with a liquid having the weight W placed only in the replacement fluid storage container, is Wr, and when each weight of B, Wf, and Wr is obtained from a numerical value measured by the scale of the blood purification apparatus $$|Wf - Wr|/W \leq 0.005 \qquad (1).$$

8. The blood purification system according to claim 7, wherein
another container is located in the second planar panel, and
the weight B is weight when the two storage containers and the another container of the second planar panel are empty.

9. The blood purification system according to claim 8, wherein the another container is connected to the replacement fluid storage container.

10. The blood purification system according to claim 7, wherein a flow path for forming a dialysate supplying tubing part for supplying a dialysate to the blood purifier is formed in the first planar panel.

11. The blood purification system according to claim 7, wherein
one end side of the soft tube is connected at an end α on the second planar panel, and the other end side is connected at an end β on the first planar panel, and
the soft tube is located so that
when an axial direction in an arbitrary portion χ in a longitudinal direction of the soft tube connecting the end α and the end β is a vector X,
a gravity direction is a vector G, and
a narrower angle formed by the vector X and the vector G is an angle θX,
at least one portion χ in which the angle θX is 70° to 110° is present,
provided that the vector X is a direction from the second planar panel toward the first planar panel.

12. The blood purification system according to claim 7, wherein
the blood purification tubing further has a replacement fluid feed pump tube and a drainage feed pump tube,
the blood purification apparatus further has a replacement fluid feed pump and a drainage feed pump for squeezing the pump tubes for feeding,
in the replacement fluid supplying tubing part, the replacement fluid feed pump tube, a replacement fluid branch duct, and a replacement fluid supply blocking part are located in this order from a blood returning tubing part or blood drawing tubing part side on a tubing having one end side connected to the blood returning tubing part or the blood drawing tubing part and the other end side connected to a replacement fluid storage part, and the replacement fluid storage container is connected to the replacement fluid branch duct,
in the drainage tubing part, the drainage feed pump tube, a drainage branch duct, and a drainage blocking part are located in this order from a drainage outlet side of the blood purifier on a tubing having one end side connected to a drainage outlet of the blood purifier and the other end side open, and the drainage storage container is connected to the drainage branch duct,
the blood purification apparatus further has a replacement fluid supply blocking valve and a drainage blocking valve for blocking the blocking parts,
a flow path in a portion near the replacement fluid feed pump tube and between an end connected to the blood returning tubing part or the blood drawing tubing part and the replacement fluid feed pump tube, and a flow path in a portion near the replacement fluid feed pump tube and between the replacement fluid feed pump tube and an end on the side connected to the replacement fluid storage part, in the replacement fluid supplying tubing part, and
a flow path in a portion near the drainage feed pump tube and between the drainage outlet of the blood purifier and the drainage feed pump tube, and a flow path in a portion near the drainage feed pump tube and between the drainage feed pump tube and an open end, in the drainage tubing part
are installed in the first planar panel,
the replacement fluid feed pump tube and the drainage feed pump tube are connected to the first planar panel, and
the replacement fluid branch duct and the drainage branch duct are installed in the first planar panel or the second planar panel.

13. The blood purification system according to claim 12, wherein
the blood purification apparatus has a heating apparatus,
the flow path in the portion near the replacement fluid feed pump tube and between the end connected to the blood returning tubing part or the blood drawing tubing part and the replacement fluid feed pump tube in the replacement fluid supplying tubing part, installed in the first planar panel, is a replacement fluid heating flow path, and at least one surface of the replacement fluid heating flow path is in contact with a heater surface of the heating apparatus.

14. The blood purification system according to claim 12, wherein the replacement fluid feed pump and the drainage feed pump are tubing pumps, and a plane of an orbit in which a roller revolves, and a planar part of the first planar panel are located at a generally right angle.

15. The blood purification system according to claim 12, wherein having a fixture for fixing a part on an inlet side and/or outlet side of any of the replacement fluid feed pump tube and the drainage feed pump tube.

16. The blood purification system according to claim 1, wherein the first planar panel is an integral plastic molding or one in which plastic moldings are bonded and integrated.

* * * * *